(12) United States Patent
Yu et al.

(10) Patent No.: US 11,066,680 B2
(45) Date of Patent: Jul. 20, 2021

(54) IL6R BLOCK CAR-T TRANSGENIC VECTOR FOR ALLEVIATING CRS, PREPARATION METHOD THEREOF

(71) Applicant: SHANGHAI UNICAR-THERAPY BIO-MEDICINE TECHNOLOGY CO., LTD, Shanghai (CN)

(72) Inventors: Lei Yu, Shanghai (CN); Liqing Kang, Shanghai (CN); Zhou Yu, Shanghai (CN); Nan Xu, Shanghai (CN)

(73) Assignee: SHANGHAI UNICAR-THERAPY BIO-MEDICINE TECHNOLOGY CO., LTD., Shanghai (CN)

( * ) Notice: Subject to any disclaimer, the term of this patent is extended or adjusted under 35 U.S.C. 154(b) by 58 days.

(21) Appl. No.: 16/464,680

(22) PCT Filed: Nov. 13, 2017

(86) PCT No.: PCT/CN2017/110654
§ 371 (c)(1),
(2) Date: May 28, 2019

(87) PCT Pub. No.: WO2018/103502
PCT Pub. Date: Jun. 14, 2018

(65) Prior Publication Data
US 2019/0292564 A1  Sep. 26, 2019

(30) Foreign Application Priority Data
Dec. 5, 2016  (CN) .......................... 201611103319.2

(51) Int. Cl.
| | |
|---|---|
| C12N 15/86 | (2006.01) |
| C07K 14/54 | (2006.01) |
| C07K 14/25 | (2006.01) |
| C12N 15/867 | (2006.01) |
| C12N 15/66 | (2006.01) |
| C07K 14/725 | (2006.01) |
| C07K 14/705 | (2006.01) |
| C07K 16/28 | (2006.01) |
| A61P 29/00 | (2006.01) |
| A61P 35/00 | (2006.01) |
| A61K 48/00 | (2006.01) |
| A61K 39/00 | (2006.01) |
| A61K 35/17 | (2015.01) |
| C12N 15/113 | (2010.01) |

(52) U.S. Cl.
CPC .............. *C12N 15/86* (2013.01); *A61K 35/17* (2013.01); *A61K 39/00* (2013.01); *A61K 48/00* (2013.01); *A61P 29/00* (2018.01); *A61P 35/00* (2018.01); *C07K 14/5412* (2013.01); *C07K 14/7051* (2013.01); *C07K 14/70517* (2013.01); *C07K 14/70521* (2013.01); *C07K 14/70578* (2013.01); *C07K 16/2803* (2013.01); *C07K 16/2866* (2013.01); *C12N 15/113* (2013.01); *C12N 15/66* (2013.01); *C12N 15/867* (2013.01); *C07K 2317/21* (2013.01); *C07K 2317/24* (2013.01); *C07K 2317/52* (2013.01); *C07K 2317/622* (2013.01); *C07K 2317/73* (2013.01); *C07K 2317/76* (2013.01); *C07K 2319/02* (2013.01); *C07K 2319/03* (2013.01); *C07K 2319/30* (2013.01); *C12N 2740/15043* (2013.01); *C12N 2760/00043* (2013.01); *C12N 2760/00051* (2013.01); *C12N 2800/107* (2013.01)

(58) Field of Classification Search
CPC ................ C12N 15/86; C07K 14/5412; C07K 14/7051; C07K 14/70517
See application file for complete search history.

(56) References Cited

FOREIGN PATENT DOCUMENTS

| | | | |
|---|---|---|---|
| CN | 105602992 A | | 5/2016 |
| CN | 105640990 A | | 6/2016 |
| CN | 105814083 A | | 7/2016 |
| CN | 105950662 | * | 9/2016 |
| CN | 105950662 A | | 9/2016 |
| CN | 107245500 | * | 10/2017 |
| WO | WO-2017172981 A2 | * | 10/2017 ........... A61K 48/005 |

OTHER PUBLICATIONS

Yelei Guo, et al. Chimeric Antigen Receptor-Modified T Cells for Solid Tumors: Challenges and Prospects, Journal of Immunology Research, Feb. 21, 2016, Article ID 3850839, 11 pages.

Fang Chen, et al. Measuring IL-6 and sIL-6R in Serum from Patients Treated with Tocilizumab and/or Siltuximab Following CAR T Cell Therapy, J Immunol Methods, vol. 434, Jul. 31, 2016.

(Continued)

*Primary Examiner* — Anoop K Singh
(74) *Attorney, Agent, or Firm* — Bayramoglu Law Offices LLC

(57) ABSTRACT

An IL6R block CAR-T transgenic vector for alleviating CRS includes: AmpR sequence containing ampicillin resistance gene (SEQ ID NO: 1); prokaryotic replicon pUC Ori sequence (SEQ ID NO: 2); virus replicon SV40 Ori sequence (SEQ ID NO: 3); eWPRE enhanced posttranscriptional regulatory element of hepatitis B virus (SEQ ID NO: 11); human EF1a promoter (SEQ ID NO: 12); lentiviral packaging cis-elements for lentiviral packaging; humanized single-chain antibody fragment IL6RscFv1 (SEQ ID NO: 21), IL6RscFv2 (SEQ ID NO: 22), or IL6RscFv3 (SEQ ID NO: 23) of human IL6R; IRES ribosome binding sequence (SEQ ID NO: 25); IL6 signal peptide (SEQ ID NO: 26); human antibody Fc segment (SEQ ID NO: 27); and chimeric antigen receptors of the second or third generation CAR for integrating recognition, transmission and initiation. A preparation method of the IL6R block CAR-T transgenic vector and an application thereof in a preparation of drugs for alleviating CRS.

10 Claims, 14 Drawing Sheets
Specification includes a Sequence Listing.

(56) References Cited

OTHER PUBLICATIONS

Wang, Lei et al. Application of Chimeric Antigen Receptor-Modified CAR-T/NK Cells in the Treatment of Multiple Myeloma. Journal of Experimental Hematology Apr. 30, 2015 23(2), ISSN:1009-2137, pp. 568-572.
Burnet FM. et al. Immunological Aspects of Malignant Disease. The Lancet, Jun. 3, 1967:1:1171-4.
Eleanor J. Cheadle, et al. CAR T Cells: Driving the Road from the Laboratory to the Clinic. Immunological Reviews 2014. vol. 257:91-106.
Porter DL, et al. Chimeric Antigen Receptor-modified T Cells in Chronic Lymphoid Leukemia. N Engl J Med Aug. 25, 2011:365(8):725-733.

* cited by examiner

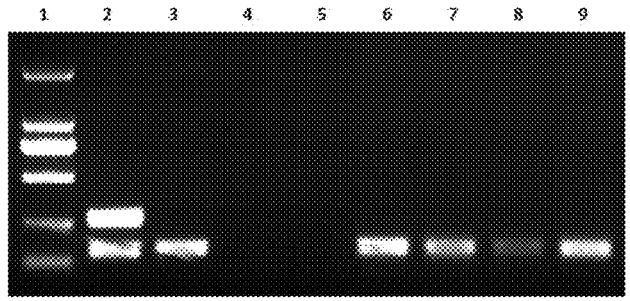

| PCR template | Products of PCR | Judgment and description |
|---|---|---|
| Positive control | a 280bp band and a 150bp band | Established positiveness |
| | no or only one band | Unestablished positiveness |
| Negative control | a 150bp band | Established negativeness |
| | no or more than 2 bands | Unestablished negativeness |
| Sample | a 280bp band and a 150bp band | Mycoplasma contamination |
| | only a 280bp band | Severe mycoplasma contamination |
| | only a 150bp band | No mycoplasma contamination |
| | no band | Insufficient quantity of cells or inhabited PCR |

FIG. 9

| Name of Sample | Actin (CT) | CAR (CT) | -ΔCt | -ΔΔCt | $2^{-\Delta\Delta Ct}$ |
|---|---|---|---|---|---|
| lvCAR19-IL6RscFv1 | 20.4502 | 30.09621 | -9.64692 | 5.76444 | 54.35868 |
| lvCAR19-IL6RscFv2 | 19.64072 | 29.24799 | -9.60727 | 5.80319 | 55.83843 |
| lvCAR19-IL6RscFv3 | 19.72143 | 29.34251 | -9.62107 | 5.78938 | 55.30658 |
| lvCAR19-scFv0 | 19.96796 | 29.55263 | -9.58467 | 5.82578 | 56.71996 |
| MOCK | 19.44765 | 34.98443 | -15.5368 | -0.12634 | 0.916156 |
| Blank | 19.89311 | 35.38357 | -15.4105 | 0 | 1 |

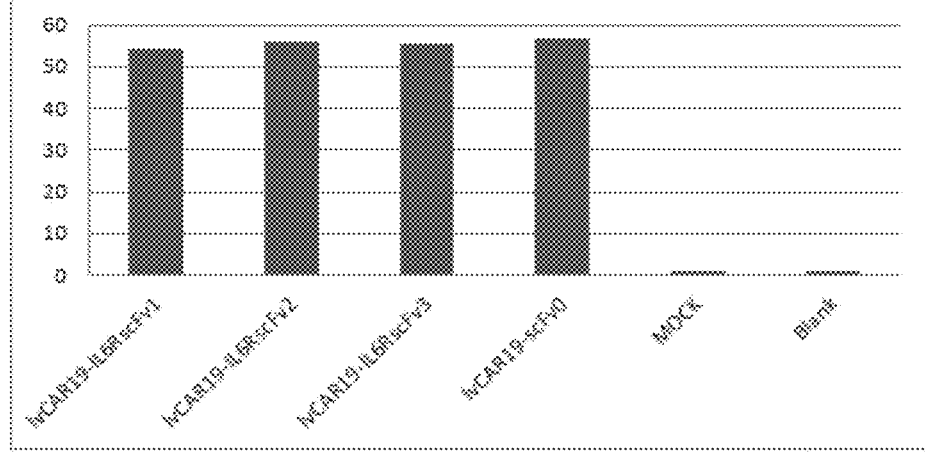

FIG. 10A

SEQUENCE LISTING

```
<160> NUMBER OF SEQ ID NOS: 68

<210> SEQ ID NO 1
<211> LENGTH: 861
<212> TYPE: DNA
<213> ORGANISM: Artificial Sequence
<220> FEATURE:
<223> OTHER INFORMATION: the sequence is synthetized

<400> SEQUENCE: 1
atgagtattc aacatttccg tgtcgccctt attccttttt ttgcggcatt ttgccttcct     60 gttttgctc acccagaaac gctggtgaaa gtaaaagatg ctgaagatca gttgggtgca    120
cgagtgggtt acatcgaact ggatctcaac agcggtaaga tccttgagag ttttcgcccc    180
gaagaacgtt ttccaatgat gagcactttt aaagttctgc tatgtggcgc ggtattatcc    240
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg gggatcatgt aactcgcctt    480
gatcgttggg aaccggagct gaatgaagcc ataccaaacg acgagcgtga ccacacgatg    540
cctgtagcaa tggcaacaac gttgcgcaaa ctattaactg gcgaactact tactctagct    600
tcccggcaac aattaataga ctggatggag gcggataaag ttgcaggacc acttctgcgc    660
```

```
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatggatgaa cgaaatagac agatcgctga gataggtgcc    840
tcactgatta agcattggta a                                              861
```

```
<210> SEQ ID NO 2
<211> LENGTH: 674
<212> TYPE: DNA
<213> ORGANISM: Artificial Sequence
<220> FEATURE:
<223> OTHER INFORMATION: the sequence is synthetized

<400> SEQUENCE: 2
cccgtagaaa agatcaaagg atcttcttga tccttttt ttctgcgcgt aatctgctgc      60
ttgcaaacaa aaaaaccacc gctaccagcg gtggtttgtt tgccggatca agagctacca   120 actcttttc cgaaggtaac tggcttcagc agagcgcaga taccaaatac tgtccttcta    180
gtgtagccgt agttaggcca ccacttcaag aactctgtag caccgcctac atacctcgct    240
ctgctaatcc tgttaccagt ggctgctgcc agtggcgata gtcgtgtct taccgggttg     300 gactcaagac gatagttacc ggataaggcg cagcggtcgg gctgaacggg gggttcgtgc    360
acacagccca gcttggagcg aacgacctac accgaactga gatacctaca gcgtgagcta    420
tgagaaagcg ccacgcttcc cgaagggaga aaggcggaca ggtatccggt aagcggcagg    480
gtcggaacag gagagcgcac gagggagctt ccagggggaa acgcctggta tctttatagt    540
cctgtcgggt ttcgccacct ctgacttgag cgtcgatttt tgtgatgctc gtcaggggg     600 cggagcctat ggaaaaacgc cagcaacgcg gccttttac ggttcctggc cttttgctgg     660
ccttttgctc acat                                                     674
```

```
<210> SEQ ID NO 3
<211> LENGTH: 147
<212> TYPE: DNA
<213> ORGANISM: Artificial sequence
<220> FEATURE:
<223> OTHER INFORMATION: the sequence is synthetized

<400> SEQUENCE: 3
atcccgcccc taactccgcc cagttccgcc cattctccgc cccatggctg actaattttt     60
tttatttatg cagaggccga ggccgcctcg gcctctgagc tattccagaa gtagtgagga   120
ggcttttttg gaggcctaga cttttgc                                       147
```

```
<210> SEQ ID NO 4
<211> LENGTH: 228
<212> TYPE: DNA
<213> ORGANISM: Artificial sequence
<220> FEATURE:
<223> OTHER INFORMATION: the sequence is synthetized

<400> SEQUENCE: 4
gtagtcttat gcaatactct tgtagtcttg caacatggta acgatgagtt agcaacatgc     60
cttacaagga gagaaaaagc accgtgcatg ccgattggtg gaagtaaggt ggtacgatcg   120
tgccttatta ggaaggcaac agacgggtct gacatggatt ggacgaacca ctgaattgcc   180
gcattgcaga gatattgtat ttaagtgcct agctcgatac aataaacg                228
```

```
<210> SEQ ID NO 5
```

```
<211> LENGTH: 180
<212> TYPE: DNA
<213> ORGANISM: Artificial sequence
<220> FEATURE:
<223> OTHER INFORMATION: the sequence is synthetized

<400> SEQUENCE: 5
ggtctctctg gttagaccag atctgagcct gggagctctc tggctaacta gggaacccac      60
tgcttaagcc tcaataaagc ttgccttgag tgcttcaagt agtgtgtgcc cgtctgttgt     120
gtgactctgg taactagaga tccctcagac ccttttagtc agtgtggaaa atctctagca     180

<210> SEQ ID NO 6
<211> LENGTH: 234
<212> TYPE: DNA
<213> ORGANISM: Artificial sequence
<220> FEATURE:
<223> OTHER INFORMATION: the sequence is synthetized

<400> SEQUENCE: 6
tgctagagat tttccacact gactaaaagg gtctgaggga tctctagtta ccagagtcac      60
acaacagacg ggcacacact acttgaagca ctcaaggcaa gctttattga ggcttaagca     120
gtgggttccc tagttagcca gagagctccc aggctcagat ctggtctaac cagagagacc     180
cagtacaagc aaaaagcaga tcttattttc gttgggagtg aattagccct tcca           234

<210> SEQ ID NO 7
<211> LENGTH: 353
<212> TYPE: DNA
<213> ORGANISM: Artificial sequence
<220> FEATURE:
<223> OTHER INFORMATION: the sequence is synthetized

<400> SEQUENCE: 7
atgggtgcga gagcgtcagt attaagcggg ggagaattag atcgcgatgg gaaaaaattc      60
ggttaaggcc agggggaaag aaaaaatata aattaaaaca tatagtatgg gcaagcaggg     120
agctagaacg attcgcagtt aatcctggcc tgttagaaac atcagaaggc tgtagacaaa     180
tactgggaca gctacaacca tcccttcaga caggatcaga gaacttaga tcattatata     240 atacagtagc aaccctctat tgtgtgcatc aaaggataga gataaaagac accaaggaag     300
ctttagacaa gatagaggaa gagcaaaaca aaagtaagac caccgcacag caa            353

<210> SEQ ID NO 8
<211> LENGTH: 233
<212> TYPE: DNA
<213> ORGANISM: Artificial sequence
<220> FEATURE:
<223> OTHER INFORMATION: the sequence is synthetized

<400> SEQUENCE: 8
aggagctttg ttccttgggt tcttgggagc agcaggaagc actatgggcg cagcctcaat      60
gacgctgacg gtacaggcca gacaattatt gtctggtata gtgcagcagc agaacaattt     120
gctgagggct attgaggcgc aacagcatct gttgcaactc acagtctggg gcatcaagca     180
gctccaggca agaatcctgg ctgtggaaag atacctaaag gatcaacagc tcc            233

<210> SEQ ID NO 9
<211> LENGTH: 489
<212> TYPE: DNA
<213> ORGANISM: Artificial sequence
<220> FEATURE:
<223> OTHER INFORMATION: the sequence is synthetized
```

-continued

<400> SEQUENCE: 9

```
tggggatttg gggttgctct ggaaaactca tttgcaccac tgctgtgcct tggaatgcta      60
gttggagtaa taaatctctg aacagattg gaatcacacg acctggatgg agtgggacag      120
agaaattaac aattacacaa gcttaataca ctccttaatt gaagaatcgc aaaaccagca     180
agaaaagaat gaacaagaat tattggaatt agataaatgg gcaagtttgt ggaattggtt     240
taacataaca aattggctgt ggtatataaa attattcata atgatagtag gaggcttggt     300
aggtttaaga atagttttg ctgtactttc tatagtgaat agagttaggc agggatattc      360
accattatcg tttcagaccc acctcccaac cccgagggga cccgacaggc ccgaaggaat     420
agaagaagaa ggtggagaga gagacagaga cagatccatt cgattagtga acggatctcg     480
acggttaac                                                              489
```

<210> SEQ ID NO 10
<211> LENGTH: 119
<212> TYPE: DNA
<213> ORGANISM: Artificial sequence
<220> FEATURE:
<223> OTHER INFORMATION: the sequence is synthetized

<400> SEQUENCE: 10

```
ttttaaaaga aaggggga ttgggggta cagtgcaggg gaaagaatag tagacataat        60
agcaacagac atacaaacta aagaattaca aaaacaaatt acaaaaattc aaaattttta    119
```

<210> SEQ ID NO 11
<211> LENGTH: 592
<212> TYPE: DNA
<213> ORGANISM: Artificial sequence
<220> FEATURE:
<223> OTHER INFORMATION: the sequence is synthetized

<400> SEQUENCE: 11

```
aatcaacctc tggattacaa aatttgtgaa agattgactg gtattcttaa ctatgttgct      60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aacccccact    240
ggttggggca ttgccaccac ctgtcagctc ctttccggga ctttcgcttt cccctccct    300
attgccacgg cggaactcat cgccgcctgc cttgcccgct gctggacagg gctcggctg     360
ttgggcactg acaattccgt ggtgttgtcg gggaatcat cgtcctttcc ttggctgctc     420
gcctgtgttg ccacctggat tctgcgcggg acgtccttct gctacgtccc ttcggccctc    480
aatccagcgg accttcctc ccgcggctg ctgccggctc tgcggcctct tccgcgtctt      540
cgccttcgcc ctcagacgag tcggatctcc ctttgggccg cctccccgcc tg            592
```

<210> SEQ ID NO 12
<211> LENGTH: 1178
<212> TYPE: DNA
<213> ORGANISM: Artificial sequence
<220> FEATURE:
<223> OTHER INFORMATION: the sequence is synthetized

<400> SEQUENCE: 12

```
gctccggtgc ccgtcagtgg gcagagcgca catcgcccac agtccccgag aagttggggg      60
gaggggtcgg caattgaacc ggtgcctaga gaaggtggcg cggggtaaac tgggaaagtg    120
```

```
atgtcgtgta ctggctccgc cttttcccg agggtggggg agaaccgtat ataagtgcag    180
tagtcgccgt gaacgttctt tttcgcaacg ggtttgccgc cagaacacag gtaagtgccg    240
tgtgtggttc ccgcgggcct ggcctcttta cgggttatgg cccttgcgtg ccttgaatta    300
cttccacctg gctgcagtac gtgattcttg atcccgagct tcgggttgga agtgggtggg    360
agagttcgag gccttgcgct taaggagccc cttcgcctcg tgcttgagtt gaggcctggc    420
ctgggcgctg gggccgccgc gtgcgaatct ggtggcacct tcgcgcctgt ctcgctgctt    480
tcgataagtc tctagccatt taaaatttt gatgacctgc tgcgacgctt ttttctggc     540 aagatagtct tgtaaatgcg ggccaagatc tgcacactgg tatttcggtt tttgggccg    600 cgggcggcga cggggcccgt gcgtcccagc gcacatgttc ggcgaggcgg ggcctgcgag    660
cgcggccacc gagaatcgga cgggggtagt ctcaagctgg ccggcctgct ctggtgcctg    720
gcctcgcgcc gccgtgtatc gccccgccct gggcggcaag gctggcccgg tcggcaccag    780
ttgcgtgagc ggaaagatgg ccgcttcccg gccctgctgc agggagctca aaatggagga    840
cgcggcgctc gggagagcgg gcgggtgagt cacccacaca aaggaaaagg ccttttccgt    900
cctcagccgt cgcttcatgt gactccactg agtaccgggc gccgtccagg cacctcgatt    960
agttctcgag cttttggagt acgtcgtctt taggttgggg ggaggggttt tatgcgatgg   1020
agtttcccca cactgagtgg gtggagactg aagttaggcc agcttggcac ttgatgtaat   1080
tctccttgga atttgcccctt tttgagtttg gatcttggtt cattctcaag cctcagacag   1140
tggttcaaag ttttttcttt ccatttcagg tgtcgtga                           1178

<210> SEQ ID NO 13
<211> LENGTH: 63
<212> TYPE: DNA
<213> ORGANISM: Artificial sequence
<220> FEATURE:
<223> OTHER INFORMATION: the sequence is synthetized

<400> SEQUENCE: 13
atggccttac cagtgaccgc cttgctcctg ccgctggcct tgctgctcca cgccgccagg    60
ccg                                                                 63

<210> SEQ ID NO 14
<211> LENGTH: 321
<212> TYPE: DNA
<213> ORGANISM: Artificial sequence
<220> FEATURE:
<223> OTHER INFORMATION: the sequence is synthetized

<400> SEQUENCE: 14
gacatccaga tgacacagac tacatcctcc ctgtctgcct ctctgggaga cagagtcacc    60
atcagttgca gggcaagtca ggacattagt aaatatttaa attggtatca gcagaaacca    120
gatggaactg ttaaactcct gatctaccat acatcaagat tacactcagg agtcccatca    180
aggttcagtg gcagtgggtc tggaacagat tattctctca ccattagcaa cctggagcaa    240
gaagatattg ccacttactt ttgccaacag ggtaatacgc ttccgtacac gttcggaggg    300
gggaccaagc tggagatcac a                                             321

<210> SEQ ID NO 15
<211> LENGTH: 45
<212> TYPE: DNA
<213> ORGANISM: Artificial sequence
<220> FEATURE:
<223> OTHER INFORMATION: the sequence is synthetized
```

<400> SEQUENCE: 15
ggtggcggtg gctcgggcgg tggtgggtcg ggtggcggcg gatct                45

<210> SEQ ID NO 16
<211> LENGTH: 360
<212> TYPE: DNA
<213> ORGANISM: Artificial sequence
<220> FEATURE:
<223> OTHER INFORMATION: the sequence is synthetized

<400> SEQUENCE: 16
gaggtgaaac tgcaggagtc aggacctggc ctggtggcgc cctcacagag cctgtccgtc    60
acatgcactg tctcaggggt ctcattaccc gactatggtg taagctggat tcgccagcct   120
ccacgaaagg gtctggagtg gctgggagta atatggggta gtgaaaccac atactataat   180
tcagctctca aatccagact gaccatcatc aaggacaact ccaagagcca agttttctta   240
aaaatgaaca gtctgcaaac tgatgacaca gccatttact actgtgccaa acattattac   300
tacggtggta gctatgctat ggactactgg ggccaaggaa cctcagtcac cgtctcctca   360

<210> SEQ ID NO 17
<211> LENGTH: 141
<212> TYPE: DNA
<213> ORGANISM: Artificial sequence
<220> FEATURE:
<223> OTHER INFORMATION: the sequence is synthetized

<400> SEQUENCE: 17
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgatatcta c                                            141

<210> SEQ ID NO 18
<211> LENGTH: 66
<212> TYPE: DNA
<213> ORGANISM: Artificial sequence
<220> FEATURE:
<223> OTHER INFORMATION: the sequence is synthetized

<400> SEQUENCE: 18
atctgggcgc ccttggccgg gacttgtggg gtccttctcc tgtcactggt tatcacccTT    60
tactgc                                                              66

<210> SEQ ID NO 19
<211> LENGTH: 126
<212> TYPE: DNA
<213> ORGANISM: Artificial sequence
<220> FEATURE:
<223> OTHER INFORMATION: the sequence is synthetized

<400> SEQUENCE: 19
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                             126

<210> SEQ ID NO 20
<211> LENGTH: 336
<212> TYPE: DNA
<213> ORGANISM: Artificial sequence
<220> FEATURE:

<223> OTHER INFORMATION: the sequence is synthetized

<400> SEQUENCE: 20

| agagtgaagt tcagcaggag cgcagacgcc cccgcgtaca agcagggcca gaaccagctc | 60 |
|---|---|
| tataacgagc tcaatctagg acgaagagag gagtacgatg ttttggacaa gagacgtggc | 120 |
| cgggaccctg agatgggggg aaagccgaga aggaagaacc ctcaggaagg cctgtacaat | 180 |
| gaactgcaga agataagat ggcggaggcc tacagtgaga ttgggatgaa aggcgagcgc | 240 |
| cggaggggca aggggcacga tggcctttac cagggtctca gtacagccac caaggacacc | 300 |
| tacgacgccc ttcacatgca ggccctgccc cctcgc | 336 |

<210> SEQ ID NO 21
<211> LENGTH: 723
<212> TYPE: DNA
<213> ORGANISM: Artificial sequence
<220> FEATURE:
<223> OTHER INFORMATION: the sequence is synthetized

<400> SEQUENCE: 21

| gacatccaga tgacccagag cccaagcagc ctgagcgcca gcgtgggtga cagagtgacc | 60 |
|---|---|
| atcacctgta gagccagcca ggacatcagc agttacctga attggtacca gcagaagcca | 120 |
| ggaaaggctc caaagctgct gatctactac acctccagac tgcactctgg tgtgccaagc | 180 |
| agattcagcg gtagcggtag cggtaccgac ttcaccttca ccatcagcag cctccagcca | 240 |
| gaggacatcg ctacctacta ctgccaacag ggtaacacgc ttccatacac gttcggccaa | 300 |
| gggaccaagg tggaaatcaa aggtggcggt ggctcgggcg tggtgggtc gggtggcggc | 360 |
| ggatctcagg tccaactgca ggagagcggt ccaggtcttg tgagacctag ccagaccctg | 420 |
| agcctgacct gcaccgtgtc tggctactca attaccagcg atcatgcctg gagctgggtt | 480 |
| cgccagccac ctggacgagg tcttgagtgg attggataca ttagttatag tggaatcaca | 540 |
| acctataatc catctctcaa atccagagtg acaatgctga gagacaccag caagaaccag | 600 |
| ttcagcctga gactcagcag cgtgacagcc gccgacaccg cggtttatta ttgtgcaaga | 660 |
| tccctagctc ggactacggc tatggactac tggggtcaag gcagcctcgt cacagtctcc | 720 |
| tca | 723 |

<210> SEQ ID NO 22
<211> LENGTH: 747
<212> TYPE: DNA
<213> ORGANISM: Artificial sequence
<220> FEATURE:
<223> OTHER INFORMATION: the sequence is synthetized

<400> SEQUENCE: 22

| gaaattgtga tgacccagag cccggcgacc ctgagcgtga gcccgggcga acgcgcgacc | 60 |
|---|---|
| attacctgcc gcgcgagcca gggcattagc agctggctgg cgtggtatca gcagaaaccg | 120 |
| ggccaggcgc cgcgcctgct gatttatggc gcgagcaccc gcgcgaccgg cattccggcg | 180 |
| cgctttagcg gcagcggcag cggcaccgat tttaccctga ccattagcag cctgcagccg | 240 |
| gaagattttg cggtgtatta ttgccagcag tatagcagct ggccgccgta cccttggc | 300 |
| cagggcacca aactggaaat taaaggtggc ggtggctcgg gcggtggtgg gtcgggtggc | 360 |
| ggcggatctg aagtgcagct ggtggaaagc ggcggcaacc tggtgcagcc gggccgcagc | 420 |
| ctgcgcctga gctgcgcggc gagcggcttt attttttgatg attatgcgat gcattgggtg | 480 |
| cgccaggcgc cgggcaaagg cctggaatgg gtgagcggca ttagctggaa cagcggcagc | 540 |

```
attggctatg cggatagcgt gaaaggccgc tttaccatta gccgcgataa cgcgaaaaac    600
agcctgtatc tgcagatgaa cagcctgcgc gcggaagata ccgcgctgta ttattgcgcg    660
aaagatggcg gcagcagctg gctgccgttt gtgtattatt atggcatgga tgtgtggggc    720
cagggcacca ccgtgaccgt gagcagc                                        747
```

<210> SEQ ID NO 23
<211> LENGTH: 744
<212> TYPE: DNA
<213> ORGANISM: Artificial sequence
<220> FEATURE:
<223> OTHER INFORMATION: the sequence is synthetized

<400> SEQUENCE: 23

```
gatattcaga tgacccagag cccgagcagc gtgagcgcga gcgtgggcga tcgcgtgacc     60
ctgagctgcc gcgcgagcca gagcattagc agcaactttg cgtggtatca gcagaaaccg    120
ggcaaagcgc cgaaactgct gatttatggc gcgagcagcc tggaaagcgg cgtgccgagc    180
cgctttagcg gcagcggcag cggcaccgat tttaccctga ccattagcag cctgcagagc    240
gaagattttg cgagctatta ttgccagcag gcgaacagct ttccgtatac ctttggccag    300
ggcaccaaac tggaaattaa aggtggcggt ggctcgggcg tggtgggtc gggtggcggc    360 ggatctgaag tgcagctggt ggaaagcggc ggcggcctgg tgcagccggg ccgcagcctg    420
cgcctgagct gcgcggcgag cggctttatt tttgatgatt atgcgatgca ttgggtgcgc    480
caggcgccgg gcaaaggcct ggaatgggtg agcggcatta gctggaacag cggcagcatt    540
ggctatgcgg atagcgtgaa aggccgcttt accattagcc gcgataacgc gaaaaacagc    600
ctgtatctgc agatgaacag cctgcgcgcg gaagataccg cgctgtatta ttgcgcgaaa    660
gatggcggca gcagctggct gccgtttgtg tattattatg gcatggatgt gtggggccag    720
ggcaccaccg tgaccgtgag cagc                                           744
```

<210> SEQ ID NO 24
<211> LENGTH: 699
<212> TYPE: DNA
<213> ORGANISM: Artificial sequence
<220> FEATURE:
<223> OTHER INFORMATION: the sequence is synthetized

<400> SEQUENCE: 24

```
ttgttctgga ttcctgcttc catcagtgat gttgtgatga cccaaactgt cagtcttgga     60
gatcaagctt ccatctcttg cagatctagt cagaaccttg tacacaacaa tggaaacacc    120
tatttatatt ggttcctgca gaagtcaggc cagtctccaa agctcctgat ttatagggct    180
tccatccgat tttctggggt cccagacagg ttcagtggca gtggatcaga gacagatttc    240
acactcaaga tcagcagagt ggaggcttat ttctgctttc aaggtacaca tgttccgtgg    300
acgttcggtg gaggcaccaa gctggaaatc aaaggtggcg gtggctcggg cggtggtggg    360
tcgggtggcg gcggatctga ggtgctgctg caacagtctg gacctgagct ggtgaagata    420
ccctgcaagg cttctggata cacattcact gactacaaca tggactggat gaagcagagc    480
catggaaaga gccttgagtg gattggagat attaatccta gagtggtaa ttccatctac    540 aaccagaagt tcaagggcaa ggccacactg actgtagaca gtcctccag cacagcctac    600 atggagctcc gcagcctgac atctgaggac actgcagtct atgactggtc tgcctggttt    660
gctttctggg gccaagggac tctggtctct gtctctgca                           699
```

<210> SEQ ID NO 25
<211> LENGTH: 575
<212> TYPE: DNA
<213> ORGANISM: Artificial sequence
<220> FEATURE:
<223> OTHER INFORMATION: the sequence is synthetized

<400> SEQUENCE: 25

| gcccctctcc ctcccccccc cctaacgtta ctggccgaag ccgcttggaa taaggccggt | 60 |
| gtgcgtttgt ctatatgtta ttttccacca tattgccgtc ttttggcaat gtgagggccc | 120 |
| ggaaacctgg ccctgtcttc ttgacgagca ttcctagggg tctttcccct ctcgccaaag | 180 |
| gaatgcaagg tctgttgaat gtcgtgaagg aagcagttcc tctggaagct tcttgaagac | 240 |
| aaacaacgtc tgtagcgacc ctttgcaggc agcggaaccc cccacctggc gacaggtgcc | 300 |
| tctgcggcca aaagccacgt gtataagata cacctgcaaa ggcggcacaa ccccagtgcc | 360 |
| acgttgtgag ttggatagtt gtggaaagag tcaaatggct cacctcaagc gtattcaaca | 420 |
| aggggctgaa ggatgcccag aaggtacccc attgtatggg atctgatctg gggcctcggt | 480 |
| gcacatgctt tacatgtgtt tagtcgaggt taaaaaacgt ctaggccccc cgaaccacgg | 540 |
| ggacgtggtt ttcctttgaa aaacacgatg ataat | 575 |

<210> SEQ ID NO 26
<211> LENGTH: 87
<212> TYPE: DNA
<213> ORGANISM: Artificial sequence
<220> FEATURE:
<223> OTHER INFORMATION: the sequence is synthetized

<400> SEQUENCE: 26

| atgaactcct tctccacaag cgccttcggt ccagttgcct tctccctggg gctgctcctg | 60 |
| gtgttgcctg ctgccttccc tgcccca | 87 |

<210> SEQ ID NO 27
<211> LENGTH: 696
<212> TYPE: DNA
<213> ORGANISM: Artificial sequence
<220> FEATURE:
<223> OTHER INFORMATION: the sequence is synthetized

<400> SEQUENCE: 27

| gaaccgaaaa gctgcgataa aacccatacc tgcccgccgt gcccggcgcc ggaactgctg | 60 |
| ggcggcccga gcgtgtttct gtttccgccg aaaccgaaag ataccctgat gattagccgc | 120 |
| accccggaag tgacctgcgt ggtggtggat gtgagccatg aagatccgga agtgaaattt | 180 |
| aactggtatg tggatggcgt ggaagtgcat aacgcgaaaa ccaaaccgcg cgaagaacag | 240 |
| tataacagca cctatcgcgt ggtgagcgtg ctgaccgtgc tgcatcagga ttggctgaac | 300 |
| ggcaaagaat ataaatgcaa agtgagcaac aaagcgctgc cggcgccgat tgaaaaaacc | 360 |
| attagcaaag cgaaaggcca gccgcgcgaa ccgcaggtgt ataccctgcc gccgagccgc | 420 |
| gaagaaatga ccaaaaacca ggtgagcctg acctgcctgg tgaaaggctt ttatccgagc | 480 |
| gatattgcgg tggaatggga aagcaacggc agccggaaa acaactataa aaccaccccg | 540 |
| ccggtgctgg atagcgatgg cagctttttt ctgtatagca aactgaccgt ggataaaagc | 600 |
| cgctggcagc agggcaacgt gtttagctgc agcgtgatgc atgaagcgct gcataaccat | 660 |
| tatacccaga aaagcctgag cctgagcccg ggcaaa | 696 |

```
<210> SEQ ID NO 28
<211> LENGTH: 123
<212> TYPE: DNA
<213> ORGANISM: Artificial sequence
<220> FEATURE:
<223> OTHER INFORMATION: the sequence is synthetized

<400> SEQUENCE: 28
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                   123

<210> SEQ ID NO 29
<211> LENGTH: 36
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 29
attcaaaatt ttatcgatgc tccggtgccc gtcagt                                36

<210> SEQ ID NO 30
<211> LENGTH: 22
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 30
tcacgacacc tgaaatggaa ga                                               22

<210> SEQ ID NO 31
<211> LENGTH: 42
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 31
ggtgtcgtga ggatccgcca ccatggcctt accagtgacc gc                         42

<210> SEQ ID NO 32
<211> LENGTH: 31
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 32
gtgtcatctg gatgtccggc ctggcggcgt g                                     31

<210> SEQ ID NO 33
<211> LENGTH: 41
<212> TYPE: DNA
```

```
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 33
cacgccgcca ggccggacat ccagatgaca cagactacat c                            41

<210> SEQ ID NO 34
<211> LENGTH: 20
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 34
tgtgatctcc agcttggtcc                                                    20

<210> SEQ ID NO 35
<211> LENGTH: 82
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 35
caagctggag atcacaggtg gcggtggctc gggcggtggt gggtcgggtg gcggcggatc        60
tgaggtgaaa ctgcaggagt ca                                                 82

<210> SEQ ID NO 36
<211> LENGTH: 21
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 36
tgaggagacg gtgactgagg t                                                  21

<210> SEQ ID NO 37
<211> LENGTH: 33
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 37
agtcaccgtc tcctcaacca cgacgccagc gcc                                     33

<210> SEQ ID NO 38
<211> LENGTH: 23
<212> TYPE: DNA
<213> ORGANISM: Artificial sequence
<220> FEATURE:
```

```
<223> OTHER INFORMATION: the sequence is synthetized
<220> FEATURE:
<221> NAME/KEY: misc_feature
<223> OTHER INFORMATION: Primer

<400> SEQUENCE: 38
gtagatatca caggcgaagt cca                                              23

<210> SEQ ID NO 39
<211> LENGTH: 33
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 39
cgcctgtgat atctacatct gggcgccctt ggc                                   33

<210> SEQ ID NO 40
<211> LENGTH: 39
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 40
tctttctgcc ccgtttgcag taaagggtga taaccagtg                             39

<210> SEQ ID NO 41
<211> LENGTH: 21
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 41
aaacggggca gaaagaaact c                                                21

<210> SEQ ID NO 42
<211> LENGTH: 40
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 42
tgctgaactt cactctcagt tcacatcctc cttcttcttc                            40

<210> SEQ ID NO 43
<211> LENGTH: 22
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer
```

<400> SEQUENCE: 43
agagtgaagt tcagcaggag cg                                          22

<210> SEQ ID NO 44
<211> LENGTH: 34
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 44 ggagagggc gtcgacttag cgaggggca gggc                              34

<210> SEQ ID NO 45
<211> LENGTH: 34
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 45
gccctgcccc ctcgctaagc ccctctccct cccc                             34

<210> SEQ ID NO 46
<211> LENGTH: 79
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 46
ccagggagaa ggcaactgga ccgaaggcgc ttgtggagaa ggagttcatg gtggcattat    60
catcgtgttt ttcaaagga                                              79

<210> SEQ ID NO 47
<211> LENGTH: 74
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 47
gttgccttct ccctggggct gctcctggtg ttgcctgctg ccttccctgc cccagacatc    60
cagatgaccc agag                                                   74

<210> SEQ ID NO 48
<211> LENGTH: 36
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 48
gcagcttttc ggttctgagg agactgtgac gaggct                                     36

<210> SEQ ID NO 49
<211> LENGTH: 74
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 49
gttgccttct ccctggggct gctcctggtg ttgcctgctg ccttccctgc cccagaaatt           60
gtgatgaccc agag                                                             74

<210> SEQ ID NO 50
<211> LENGTH: 36
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 50
gcagcttttc ggttcgctgc tcacggtcac ggtggt                                     36

<210> SEQ ID NO 51
<211> LENGTH: 74
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 51
gttgccttct ccctggggct gctcctggtg ttgcctgctg ccttccctgc cccagatatt           60
cagatgaccc agag                                                             74

<210> SEQ ID NO 52
<211> LENGTH: 36
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 52
gcagcttttc ggttcgctgc tcacggtcac ggtggt                                     36

<210> SEQ ID NO 53
<211> LENGTH: 76
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 53
gttgccttct ccctggggct gctcctggtg ttgcctgctg ccttccctgc cccattgttc    60
tggattcctg cttcca    76

<210> SEQ ID NO 54
<211> LENGTH: 36
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 54
gcagcttttc ggttctgcag agacagagac cagagt    36

<210> SEQ ID NO 55
<211> LENGTH: 23
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 55
gaaccgaaaa gctgcgataa aac    23

<210> SEQ ID NO 56
<211> LENGTH: 38
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 56
ctagcaatct agaggttatt tgcccgggct caggctca    38

<210> SEQ ID NO 57
<211> LENGTH: 21
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 57
cctttccggg actttcgctt t    21

<210> SEQ ID NO 58
<211> LENGTH: 20
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 58
gcagaatcca ggtggcaaca                                               20

<210> SEQ ID NO 59
<211> LENGTH: 21
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 59
catgtacgtt gctatccagg c                                             21

<210> SEQ ID NO 60
<211> LENGTH: 21
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 60
ctccttaatg tcacgcacga t                                             21

<210> SEQ ID NO 61
<211> LENGTH: 21
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 61
gacttgtggg gtccttctcc t                                             21

<210> SEQ ID NO 62
<211> LENGTH: 21
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 62
gcagctacag ccatcttcct c                                             21

<210> SEQ ID NO 63
<211> LENGTH: 19
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 63
ggattcaatg aggagactt                                                19

```
<210> SEQ ID NO 64
<211> LENGTH: 18
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 64
atctgttctg gaggtact                                              18

<210> SEQ ID NO 65
<211> LENGTH: 22
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 65
gacattggaa atgtgaacat gt                                         22

<210> SEQ ID NO 66
<211> LENGTH: 19
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 66
cacagctggg gtttggtga                                             19

<210> SEQ ID NO 67
<211> LENGTH: 22
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 67
gacattggaa atgtgaacat gt                                         22

<210> SEQ ID NO 68
<211> LENGTH: 19
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 68
cacagctggg gtttggtga                                             19
```

IL6R BLOCK CAR-T TRANSGENIC VECTOR FOR ALLEVIATING CRS, PREPARATION METHOD THEREOF

CROSS REFERENCE TO THE RELATED APPLICATIONS

This application is the national phase entry of International Application No. PCT/CN2017/110654, filed on Nov. 13, 2017, which is based upon and claims priority to Chinese Patent Application No. 201611103319.2, filed on Dec. 5, 2016, the entire contents of which are incorporated herein by reference.

TECHNICAL FIELD

This invention belongs to the field medical biology, specifically relating to a vector, especially a IL6R block CAR-T transgenic vector for alleviating CRS. Also, this invention relates to the preparation method and application of the vector.

BACKGROUND

The theoretical basis of tumor immunotherapy is that the immune system can identify tumor-associated antigens and regulate the body to attack tumor cells (highly specific cytolysis). In the 1950s, Burnet and Thomas made the theory of "immunological surveillance" that holds that mutational tumor cells that often occur in the body can be identified and eliminated by the immune system, laying a theoretical foundation for tumor immunotherapy [Burnet F M. Immunological aspects of malignant disease. Lancet, 1967; 1: 1171-4]. Then, a host of tumor immunotherapies, including cytokine therapy, monoclonal antibody therapy, adoptive immunotherapy and vaccine therapy, have been applied to clinical practice.

In 2013, CAR-T, a more advanced tumor immunotherapy, was successfully put to clinical use, and showed unprecedented clinical effects. CAR-T is short for Chimeric Antigen Receptor T-Cell Immunotherapy. Clinically, the most leading CAR-T is Novartis' CLT019. For patients with refractory-relapsed acute lymphoblastic leukemia and treated with CLT019, the six-month tumor progression-free survival rate can reach 67%, and the longest response time can be more than two years. By cooperating with hospitals, Shanghai Unicar-Therapy Bio-Medicine Technology Co., Ltd., a Shanghai-based company, treated 36 patients with refractory-relapsed acute lymphoblastic leukemia, among whom 24 as a percentage of 66.6% experienced complete remission. It's a subversive breakthrough in anti-cancer research. CAR-T may be one of the therapies that are the most likely to cure cancer, and was named the best in top 10 breakthroughs of science and technology 2013 by the journal Science.

Although CAR-T is significantly effective, there will be a special clinical syndrome in the treatment, which is usually featured by fever, hypotension, chills and neurological symptoms related to markedly elevated levels of cytokines in serum, and is called Cytokine Release Syndrome (CRS). The mechanism of the CRS is that after the binding of antigen binding with T cell receptors, T cells are activated and release a series of cytokines including IL-6, resulting in a systemic inflammatory response (see FIG. 1A for the signal path of IL-6), which, if not treated timely, will lead to a series of symptoms including lung infection, abnormal blood coagulation index, abnormal liver function, damage to vital organs, and even cause death as a result of pulmonary edema.

At present, inflammatory response can be clinically inhibited by intravenously injecting anti-histamine drugs (such as chlorphenamine maleate) or corticosteroids (such as hydrocortisone), but correspondingly, the killing effect of CAR-T cells on tumors is also inhibited, making such patients have a higher rate of palindromia and affecting the efficacy of CAR-T.

A more viable option is to use commercialized tocilizumab (ACTEMRA®) to control the extent of CRS. Tocilizumab is a humanized IL-6 receptor monoclonal antibody, and the specific binding of tocilizumab with IL-6 receptor can block IL-6 signal transduction, to reduce acute phase reactants, products of hepcidin, B cell activation, bone resorption and cartilage transformation, and inhibiting the differentiation of T lymphocytes into Th17 cells to effectively control inflammatory response. However, tombuzumab is very costly. The price of a piece of tocilizumab for 10 kg body weight of tombuzumab is about RMB 2,000, and an adult patient usually needs 5 pieces at a time, which is hard for ordinary families to afford.

Therefore, how to use low-cost methods to control or alleviate the occurrence of CRS without affecting the efficacy of CAR-T has become a technical problem in the field.

SUMMARY

One of the technical problems to be solved by the invention is to provide a IL6R block CAR-T transgenic vector for alleviating CRS. First of all, it saves the cost and the expensive cost of purchasing antibody drugs. Secondly, it avoids the problem of low delivery efficiency of scFv gene in vivo. Thirdly, the IL6R scFv gene transduced by lentivirus can effectively utilize the intracellular protein translation system and express a large number of corresponding IL6R scFv. Through fluid circulation, good IL6R blocking effect can be achieved, without affecting the curative effect of CAR-T.

The second technical problem to be solved by the invention is to provide a preparation method of the vector.

The third technical problem to be solved by the invention is to provide the application of the vector.

To solve the above technical problems, the invention adopts the following technical scheme:

In one aspect of the invention, a IL6R block CAR-T transgenic vector for alleviating CRS is provided, including:

AmpR sequence of ampicillin-resistant gene was amplified for the target bacterial strain, as shown in SEQ ID NO: 1;

Prokaryotic replicon pUC Ori sequence for plasmid replication, as shown in SEQ ID NO: 2;

SV40 Ori sequence of viral replicator used to enhance replication in eukaryotic cells, as shown in SEQ ID NO: 3;

eWPRE enhanced posttranscriptional regulatory element of Groundhog hepatitis B virus for enhancing the expression efficiency of transgene, as shown in SEQ ID NO: 11;

Human EF1α promoter for eukaryotic transcription of chimeric antigen receptor genes, as shown in SEQ ID NO: 12;

Lentivirus packaging cis-elements for lentivirus packaging;

The humanized single chain antibody fragment of human IL6R is IL6RscFv1 as shown in SEQ ID NO: 21, or IL6RscFv2 as shown in SEQ ID NO: 22, or IL6RscFv3 as shown in SEQ ID NO: 23;

IRES ribosome binding sequence for co-transcription and expression of proteins, as shown in SEQ ID NO: 25;

IL6 signal peptide, as shown in SEQ ID NO: 26;

Human antibody Fc segment, as shown in SEQ ID NO: 27;

And chimeric antigen receptors for the second or third generation of CAR, which integrates recognition, transmission and initiation.

As the preferred technical scheme of the invention, the humanized single chain antibody fragment of the human IL6R is IL6RscFv1 as shown in SEQ ID NO: 21.

The cis-component of the lentivirus packaging can adopt the second generation lentivirus vector or the third generation lentivirus vector, and the third generation lentivirus vector can be optimized. The second generation lentivirus vector includes: lentivirus 5 terminal LTR as shown in SEQ ID NO: 5, lentivirus 3 terminal Self-Inactivating LTR as shown in SEQ ID NO: 6, Gag cis-element as shown in SEQ ID NO: 7, RRE cis-element as shown in SEQ ID NO: 8, env cis-element as shown in SEQ ID NO: 9, cPPT cis-element as shown in SEQ ID NO: 10. The third-generation lentiviral vectors include: lentivirus 5 terminal LTR as shown in SEQ ID NO: 5, lentivirus 3 terminal self-Inactivating LTR as shown in SEQ ID NO: 6, Gag cis-element as shown in SEQ ID NO: 7, RRE cis-element as shown in SEQ ID NO: 8, env cis-element as shown in SEQ ID NO: 9, cPPT cis-element as shown in SEQ ID NO: 10, and RSV promoter as shown in SEQ ID NO: 4.

As the preferred technical scheme of the invention, the chimeric antigen receptors for the second generation CAR comprising: CD8 leader chimeric receptor signal peptide shown in SEQ ID NO: 13, CD19 single chain antibody fragment light chain VL shown in SEQ ID NO: 14, Optimal Linker C shown in SEQ ID NO: 15, CD19 single chain antibody fragment heavy chain VH shown in SEQ ID NO: 16, CD8 Hinge chimeric receptor hinges as shown in SEQ ID NO: 17, CD8 Transmembrane chimeric receptor transmembrane regions as shown in SEQ ID NO: 18, CD137 chimeric receptor costimulatory factors as shown in SEQ ID NO: 19, and TCR chimeric receptor T cell activation domains as shown in SEQ ID NO: 20. The chimeric antigen receptors for the three generations of CAR, which are used for recognition, transmission and initiation, include CD8 leader chimeric receptor signal peptide shown in SEQ ID NO: 13, CD19 single chain antibody fragment light chain VL shown in SEQ ID NO: 14, Optimal Linker C shown in SEQ ID NO: 15, CD19 single chain antibody fragment heavy chain VH shown in SEQ ID NO: 16, CD8 Hinge chimeric receptor hinges shown in SEQ ID NO: 17, CD8 Transmembrane chimeric receptor transmembrane region as shown in SEQ ID NO: 18, CD137 chimeric receptor costimulatory factor as shown in SEQ ID NO: 19, TCR chimeric receptor T cell activation domain as shown in SEQ ID NO: 20, and CD28 chimeric receptor costimulatory factor as shown in SEQ ID NO: 28.

As the preferred technical scheme of the invention, the eWPRE enhanced posttranscriptional regulatory element of Groundhog hepatitis B virus has six nucleotide enhanced mutations, specifically g. 396G>A, g. 397C>T, g. 398T>C, g. 399G>A, g. 400A>T, g. 411A>T.

In the second aspect of the invention, a preparation method of a IL6R block CAR-T transgenic vector is provided, including the following steps:

(1) AmpR sequence containing ampicillin resistance gene as shown in SEQ ID NO: 1, prokaryotic replicon pUC Ori sequence as shown in SEQ ID NO: 2, virus replicon SV40 Ori sequence as shown in SEQ ID NO: 3, lentivirus packaging cis-element for lentivirus packaging, and eWPRE enhanced posttranscriptional regulatory element of Groundhog hepatitis B virus as shown in SEQ ID NO: 11 were stored on lentivirus skeleton plasmid.

(2) The human EF1α promoter as shown in SEQ ID NO: 12 and chimeric antigen receptors of the second or third generation CAR used for recognition, transmission and initiation were combined into the second or third generation CAR design scheme. The recombinant lentivirus plasmids designed by the second or third generation CAR were cloned into lentivirus skeleton plasmids by digestion, ligation and recombination;

(3) The humanized single-chain antibodies IL6R scFv1, IL6R scFv2, or IL6R scFv3, IRES ribosome binding sequence, IL6 signal peptide and human antibody Fc fragment of human IL6R were cloned into recombinant lentiviral plasmids to obtain the recombinant lentiviral plasmids pCARmm-IL6R scFv1, pCARmm-IL6R scFv2, or pCARmm-IL6R scFv3;

(4) The recombinant lentiviral plasmids pCARmm-IL6RscFv1, pCARmm-IL6RscFv2, or pCARmm-IL6RscFv3 were transfected into HEK293T/17 cells with lentiviral packaging plasmids pPac-GP, pPac-R and membrane protein pEnv-G respectively. After gene transcription in HEK293T/17 cells, the recombinant lentivirus vector packaged successfully will be released into the cell culture supernatant, and the supernatant containing the recombinant lentivirus vector will be collected;

(5) The supernatant of recombinant lentivirus was purified by column purification with filtration, adsorption and elution, and the recombinant lentivirus vectors were obtained respectively.

As the preferred technical scheme of the invention, in step (3), the expression of the whole CAR gene is started by human EF1 alpha promoter; the CAR protein locates on the surface of cell membrane, recognizes CD19 antigen, stimulates T cell proliferation and cytokine secretion, and activates the expression of downstream signaling pathway; when scFv region binds to CD19 antigen, signal is transmitted to cells through chimeric receptor, which produces a series of biological effects, such as T cell proliferation, increased cytokine secretion, increased secretion of anti-apoptotic protein, delayed cell death, and lysis of target cells; the fusion protein of IL6RscFv and Fc is co-expressed by IRES ribosome binding sequence and secreted to extracellular space under the guidance of IL6 signal peptide. By binding with IL6R, the binding of IL-6 and IL6R was blocked, thus the signal pathway of IL6 was blocked, thereby inhibiting CRS.

As the preferred technical scheme of the invention, in step (5), the filtration step is to control the volume of supernatant from 200 ml to 2000 ml, the vacuum degree from −0.5 MPA to 0.9 MPA to prevent the loss of vector caused by blockage. The adsorption step is to control the PH value of solution from 6 to 8 and prevent the vector from inactivating due to the change of PH, and the elution step is to control the ionic strength of eluent from 0.5M to 1.0M and prevent the change of ionic strength leading to incomplete elution or inactivation of vector.

In the third aspect of the invention, the application of the above vectors in the preparation of drugs for alleviating CRS is provided.

Compared with the existing technology, the invention has the following beneficial effects:

The invention has the human EF1α promoter start the whole CAR genetic expression by preparing and transferring into recombinant lentiviral vectors the IL6 signal peptide, the single chain antibody of human IL6R, the IRES ribosome binding sequence, the human antibody Fc fragment, the human EF1α promoter, the CD8 leader chimeric receptor signal peptide, the CD19 single chain antibody light chain VL, the Optimal Linker C, the CD19 single-chain antibody heavy chain VH, the CD8 Hinge chimeric receptor hinge, the CD8 Transmembrane chimeric receptor transmembrane region, the CD137 chimeric receptor co-stimulatory factor, and the TCR chimeric receptor T cell activation domain. The CAR protein locates on the surface of cell membrane, recognizes CD19 antigen, stimulates T cell proliferation and cytokine secretion, and activates the expression of downstream signaling pathway; when scFv region binds to CD19 antigen, signal is transmitted to cells through chimeric receptor, which produces a series of biological effects, such as T cell proliferation, increased cytokine secretion, increased secretion of anti-apoptotic protein, delayed cell death, and lysis of target cells; the fusion protein of IL6RscFv and Fc is co-expressed by IRES ribosome binding sequence and secreted to extracellular space under the guidance of IL6 signal peptide. By binding with IL6R, the binding of IL-6 and IL6R was blocked, thus the signal pathway of IL6 was blocked, thereby inhibiting CRS.

The blocking regimen adopted by the invention can be applied to the second or third generation of CAR design. Compared with the second design of the same, the third generation of CAR design adds CD28 chimeric receptor costimulatory factor (SEQ ID NO: 28), which, according to literature report, has stronger signal amplification [Eleanor J. Cheadle, et al. CAR T cells: driving the road from the laboratory to the clinic. Immunological Reviews 2014. Vol. 257: 91-106].

The lentiviral vector column purification system (as shown in FIG. 7) used in the invention is a lentivirus scale production process developed by the applicant (which has been disclosed in the patent for invention A CAR-T Transgenic Vector Based on Replication-Defective Recombinant Lentivirus and the Preparation Method and Application Thereof applied for on Mar. 17, 2016). Common ultracentrifugation or high-speed centrifugation methods use the principle of centrifugal sedimentation to separate lentivirus particles, with which many impurities with similar sedimentation coefficients will inevitably remain and subsequent experiments will be affected adversely. Moreover, complicated tube loading, cumbersome operation and multiple conversion of containers bring more chances for contamination, while the lentiviral vector column purification process developed by the company is operated by semi-automation, and the whole process is completed in the 100-level experimental area, avoiding the cumbersomeness, errors and contamination probability of manual operation and making recovered lentiviral vector completely up to clinical standard in endotoxin, *Mycoplasma*, host DNA residual and other indicators. The development of a fully automated purification instrument may be followed up subsequently.

The CAR design adopted by the invention can also be applied to the second generation of lentivirus vector structure (which has been disclosed in the patent for invention A CAR-T Transgenic Vector Based on Replication-Defective Recombinant Lentivirus and the Preparation Method and Application Thereof applied for on Mar. 17, 2016). The major difference in structure between the second and third generations of lentivirus vector (as shown in FIG. 2B) is that in the third generation of lentivirus vector, the U3 area in the second generation of 5'LTR is replaced with the RSV promoter, so that the dependence of U3 transcription on Tat protein is eliminated, removing Tat sequences from lentiviral structural genes and improving the level and persistence of lentiviral genome transcription. Since the major difference between the second and third generations of lentivirus vector is in gene transcription, the CAR design employed by the invention can be applied to the two generations of lentivirus vector. The preferable option for the vector skeleton used in the invention is the third generation lentivirus vector (as shown in FIG. 2A) (which has been disclosed in the patent for invention A CAR-T Transgenic Vector Based on Replication-Defective Recombinant Lentivirus and the Preparation Method and Application Thereof applied for on Mar. 17, 2016). In the 3'SIN LTR, the U3 region is removed, eliminating the possibility of self-replication of the lentivirus vector, and greatly improving the security. The cPPT and WPRE elements were added to improve the transduction efficiency and the expression efficiency of the transgene. RSV promoter was used to ensure the continuous and efficient transcription of core RNA in the packaging of lentiviral vectors, and EF1a promoter was used to make CAR gene continuously expressed in human body for a long time.

The third generation of lentivirus skeleton plasmid developed the applicant (which has been disclosed in the patent for invention A CAR-T Transgenic Vector Based on Replication-Defective Recombinant Lentivirus and the Preparation Method and Application Thereof applied for on Mar. 17, 2016) employs enhanced WPRE components, which, compared with the WPRE components employed by Carl H. June and others at Pennsylvania State University (Porter D L, Levine B L, Kalos M, Bagg A, June C H. Chimeric antigen receptormodified T cells in chronic lymphoid leukemia. N Engl J Med 2011; 365:725-33.) has the enhanced mutation of 6 nucleotides (g.396G>A, g.397C>T, g.398T>C, g.399G>A, g.400A>T, g.411A>T), and can enhance the polyadenylation of primary transcription products, increase the content of mRNA in cells, and improve transgenic expression efficiency.

Lentivirus packaging system used in the invention is a four-plasmid packaging system without helper virus (which has been disclosed in the patent for invention A CAR-T Transgenic Vector Based on Replication-Defective Recombinant Lentivirus and the Preparation Method and Application Thereof applied for on Mar. 17, 2016), which produces recombinant lentiviral vectors through the co-transfection of four plasmids into HEK293T/17 cells. The recombined lentiviral vector is a single-sue replication-defective vector, which can integrate the exogenous fragments into host gene, cannot be replicated and propagated, greatly improving safety.

The invention employs a scFv blocking technology for IL-6R. Composed of the heavy chain and light chain variable regions of antibody by linking 15-20 short peptides of amino acid, the single-chain antibody fragment (scFv) can better retain its affinity for antigen, and has the characteristics of small molecular weight, strong penetrability, weak antigenicity, etc. The human IL6R blocking single-chain antibody design employed by the invention can be overexpressed in T cells and secreted into extracellular space, and block the binding of IL-6 with IL6R and the activation of IL6 signaling pathway, effectively. In the T-cell killing experiment, QPCR test shows that the design can effectively inhibit the transcription level of the mRNA of C-reactive protein in PBMC, and reduce the content of C-reactive protein in cell culture supernatant. The IL-6R blocking effect evaluation experiment proves that the vector of the invention can inhibit the IL-6 signaling pathway in vivo, alleviating the symptoms of CRS.

The scFv fragment and the Fc fragment of antibody used in the invention are both humanized, can effectively reduce the production of human anti-mouse antibodies (HAMA) in vivo, and improve the half-life period and effects of scFv.

The Linker design of the scFv fragment used in the invention (which has been disclosed in the patent for invention A CAR-T Transgenic Vector Based on Replication-Defective Recombinant Lentivirus and the Preparation Method and Application Thereof applied for on Mar. 17, 2016) can markedly improve cytokine secretion as well as the killing effects and clinical treatment effects of CAR-T cells in vitro.

The invention adopts the action mode of IL6R scFv (as shown in FIG. 1B). First of all, it saves the cost and the expensive cost of purchasing antibody drugs. Secondly, it avoids the problem of low delivery efficiency of scFv gene in vivo. Thirdly, the IL6R scFv gene transduced by lentivirus can effectively utilize the intracellular protein translation system and express a large number of corresponding IL6R scFv. Through fluid circulation, good IL6R blocking effect can be achieved. The invention screens a series of bioinformatics information such as gene sequence and amino acid sequence of IL6R antibody, predicts the variable regions of heavy and light chains of IL6R scFv, analyses the secondary structure of IL6R scFv combination and its physicochemical properties, determines the affinity constants of IL6R scFv by soluble expression and indirect ELISA, from which selects three scFv for cell function level detection. Finally, IL6RscFv1 was determined as the best choice and may enter the clinical research stage in the future. The recombinant lentivirus vector skeleton of the invention can carry different therapeutic genes and be widely used in the field of adoptive cell therapy, and can carry IL6R scFv gene and be used to block IL6R. The recombinant lentivirus vector of the invention can express CD19 chimeric antigen receptor on human T lymphocyte, guide and activate the killing effect of T lymphocyte on CD19 positive cells, and is clinically used to treat B lymphocytic leukemia, B lymphoma and multiple myeloma. The scFv expressing IL6R in human T lymphocyte can effectively block IL6R and its signaling pathway, and can be clinically used to alleviate CRS. It can be seen that the invention control or alleviate the occurrence of CRS with lost-cost methods and without prejudice to the effects of CAR-T, solving the technical problems in the field and achieving unexpected technical effects.

The IL6R single chain antibody fragment expression frame and its gene expression products described by the invention can be used not only to eliminate or alleviate CRS in the treatment of ALL with CAR-T (CD19-CAR-T), but also to alleviate CRS caused in the treatment of all kinds of tumors such as pancreatic cancer, brain glioma and myeloma with CAR-T, and even to alleviate CRS caused by other kinds of treatment.

BRIEF DESCRIPTION OF THE DRAWINGS

FIG. 4A is a prediction map of the lentiviral skeleton plasmid pLenti-3G Basic2, where lane 1 is the Cla I+BamH I enzyme digestion prediction of pLenti-3G Basic2, and the band is from top to bottom in sequence of 5854 bp; lane 2 is predicted by 1 kb DNA ladder Marker, and the bands are from top to bottom in sequence: 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; and FIG. 4B is an enzyme cut agarose gel electrophoresis map of lentiviral skeleton plasmid pLenti-3G Basic2, where lane 1 is the result of Cla I+BamH I enzyme electrophoresis of pLenti-3 G Basic2; lane 2 is the electrophoresis result of 1 KB DNA ladder Marker;

FIG. 5A is a prediction map of the recombinant lentiviral plasmid pCAR19-Basic2, where lane 1 is 1 kb DNA ladder Marker, and the bands are from top to bottom in sequence: 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; lane 2 is Nde I+Hpa I enzyme digestion prediction of pCAR19-Basic2, and the bands from top to bottom are: 6511 bp and 2014 bp; and FIG. 5B is the enzyme digestion agarose gel electrophoresis diagram of recombinant lentiviral plasmid pCAR19-Basic2, where lane1 is the electrophoresis result of 1 kb DNA ladder Marker; lane 2 is the Nde I+Hpa I enzyme digestion electrophoresis result of pCAR19-Basic2;

FIG. 6A is pCAR19-IL6RscFv1's enzyme prediction map, where lane1 is 1 kb DNA ladder Marker, and the bands are from top to bottom in sequence: 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; lane2 is ApaL I enzyme digestion prediction of pCAR19-IL6RscFv1, and the bands from top to bottom are 4230 bp, 2137 bp, 1726 bp, 1246 bp, 1054 bp, 497 bp; FIG. 6B is enzyme digestion agarose gel electrophoresis of pCAR19-IL6RscFv1, where lane1 is the electrophoretic result of 1 kb DNA ladder Marker, and lane2 is the result of ApaL I enzyme digestion electrophoresis of pCAR19-IL6RscFv1; FIG. 6C is the enzyme digestion prediction map of pCAR19-IL6RscFv2, where lane1 is 1 kb DNA ladder Marker, and the bands from top to bottom are in sequence: 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; lane2 is Kpn I enzyme digestion prediction of pCAR19-IL6RscFv2, and the bands from top to bottom are in sequence: 8335 bp, 2555 bp; FIG. 6D is enzyme digestion agarose gel electrophoresis diagram of pCAR19-IL6RscFv2, where lane1 is the electrophoresis result of 1 kb DNA ladder Marker; lane2 is the Kpn I enzyme digestion electrophoresis result of pCAR19-IL6RscFv2; FIG. 6E is the diagram is the enzyme digestion prediction map of pCAR19-IL6RscFv3, where lane1 is 1 kb DNA ladder Marker, and the bands are from top to bottom in sequence: 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; lane2 is Pvu II enzyme digestion prediction of pCAR19-IL6RscFv3, and bands from top to bottom are in sequence: 7703 bp, 2364 bp, 823 bp; FIG. 6F is the enzyme digestion agarose gel electrophoresis of pCAR19-IL6RscFv3, where lane1 is the electrophoresis result of 1 kb DNA ladder Marker, and lane2 is the Pvu II enzyme digestion electrophoresis result of pCAR19-IL6RscFv3; FIG. 6G is the enzyme digestion prediction map of pCAR19-scFv0, where lane1 is 1 kb DNA ladder Marker, and bands from top to bottom are in sequence: 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; lane2 is Sac II enzyme digestion prediction of pCAR19-scFv0, and the bands from top to bottom are: 5577 bp, 3835 bp, 895 bp, 347 bp; and FIG. 6H is an enzyme digestion agarose gel electrophoresis map of pCAR19-scFv0, where lane1 is the electrophoresis result of 1 kb DNA ladder Marker, and lane2 is the Sac II enzyme digestion electrophoresis of pCAR19-scFv0.

FIG. 9 is a schematic diagram of *Mycoplasma* detection results of different purification methods of recombinant lentivirus vectors in embodiment 2 of the invention, where lane 1 is DL2000 marker, and the bands from top to bottom in sequence: 2 kb, 1 kb, 750 bp, 500 bp, 250 bp and 100 bp; lane 2 is a positive control; lane 3 is a negative control; lane 4 is PBS; lane 5 is water; lane 6 is 1vCAR19-IL6RscFv1; lane 7 is 1vCAR19-IL6RscFv2; lane8 is 1vCAR19-IL6RscFv3; lane9 is 1vCAR19-scFv0;

FIGS. 10A and 10B are histograms of the relative expression of mRNA in embodiment 3 of the invention, where FIG. 10A is a schematic diagram of RT-QPCR results, indicating that CAR gene is highly transcribed in PBMC cells; and FIG. 10B is a schematic diagram of RT-QPCR results, indicating that scFv gene is highly transcribed in PBMC cells;

in FIG. 11A, M is protein Marker, lane 1 is empty PBMC cell, lane 2 is control virus MOCK, lane 3 is 1vCAR19-IL6RscFv1, lane 4 is 1vCAR19-IL6RscFv2, lane 5 is 1vCAR19-IL6RscFv3, lane 6 is 1vCAR19-scFv0; and FIG. 11B is an internal reference band of beta-actin;

DETAILED DESCRIPTION OF THE EMBODIMENTS

Figure 1A:
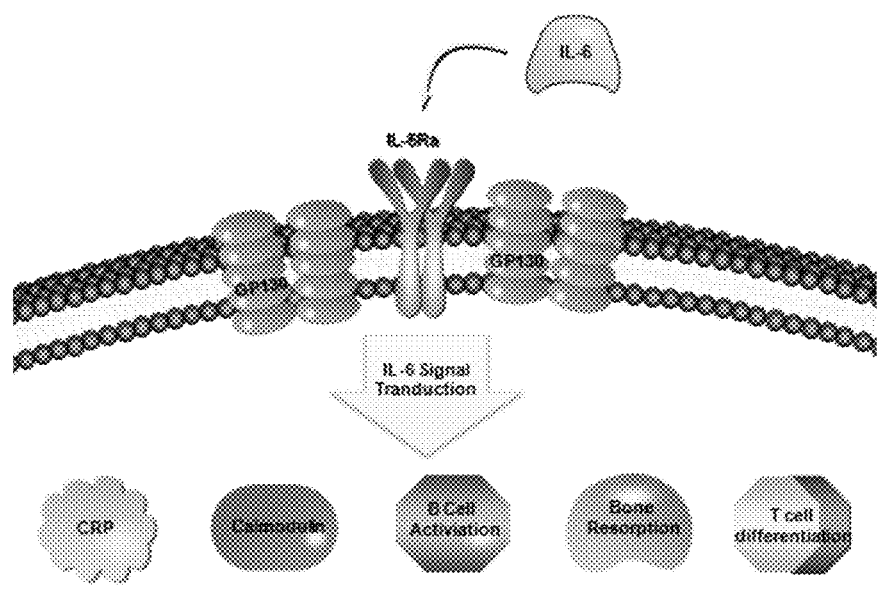
FIG. 1A is a schematic diagram of the IL-6 signaling pathway of the invention.
Figure 1B:
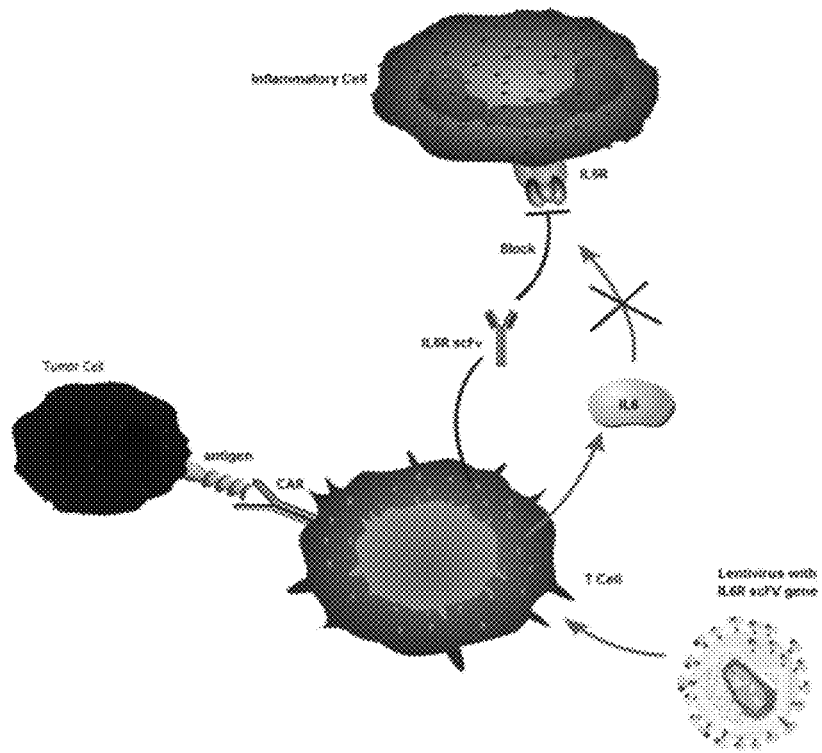
FIG. 1B is a schematic diagram of the mode of action of the IL6R scFv of the invention.
Figure 2A:
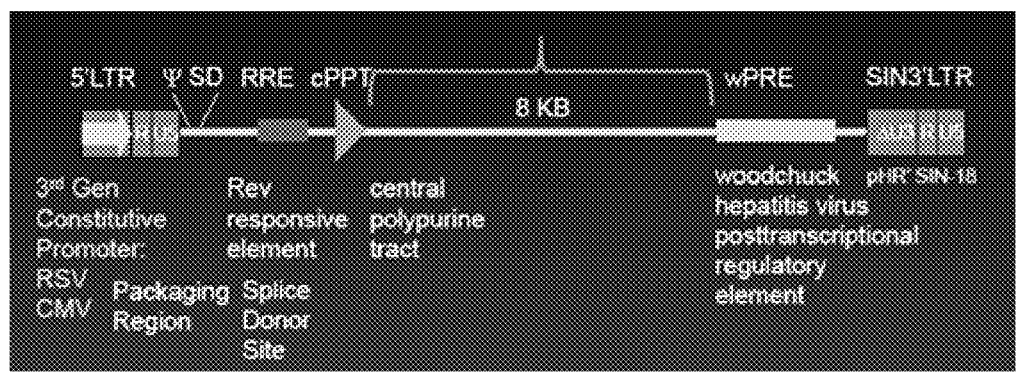
FIG. 2A is a schematic diagram of the structure of the third generation lentiviral vector adopted by the invention.
Figure 2B:
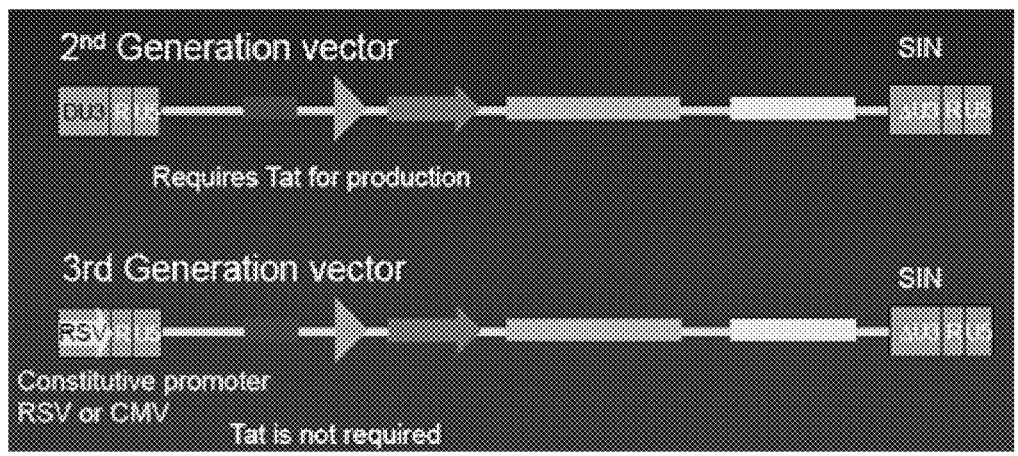
FIG. 2B is a schematic diagram of the structure comparison of the second and third generation lentiviral vectors.

The invention is further described below in connection with specific implementation methods. It should be understood that the specific implementation methods described herein are expressed by way of examples and are not constrained by the invention. Without departing from the scope of the invention, the main features of the invention can be used in various implementation methods.

Embodiment 1 to Construct Recombinant Lentiviral Vector

I. Materials

1. Lentiviral cytoskeleton plasmid pLenti-3 G Basic2, lentiviral packaging plasmid pPac-GP, pPac-R and membrane protein plasmid pEnv-G, HEK293T/17 cells, homologous recombinase, Oligo Annealing Buffer were provided by Shiao (Shanghai) Biotech Co., Ltd.;

2. Primers: Designed according to the principle of primer design, the primers required for amplification of DNA fragments and target sites were synthesized by Shanghai-based biotechnology companies, specifically as follows:

```
EF1α-F:
                                      (SEQ ID NO: 29)
5'-ATTCAAAATTTTATCGATGCTCCGGTGCCCGTCAGT-3'

EF1α-R:
                                      (SEQ ID NO: 30)
5'-TCACGACACCTGAAATGGAAGA-3'

CD8 leader-F:
                                      (SEQ ID NO: 31)
5'-GGTGTCGTGAGGATCCGCCACCATGGCCTTACCAGTGACCGC-3'

CD8 leader-R:
                                      (SEQ ID NO: 32)
5'-GTGTCATCTGGATGTCCGGCCTGGCGGCGTG-3'

VL-F:
                                      (SEQ ID NO: 33)
5'-CACGCCGCCAGGCCGGACATCCAGATGACACAGACTACATC-3'

VL-R:
                                      (SEQ ID NO: 34)
5'-TGTGATCTCCAGCTTGGTCC-3'

OLC-VH-F:
                                      (SEQ ID NO: 35)
5'-CAAGCTGGAGATCACAGGTGGCGGTGGCTCGGGCGGTGGTGGGTCGG

GTGGCGGCGGATCTGAGGTGAAACTGCAGGAGTCA-3'

VH-R:
                                      (SEQ ID NO: 36)
5'-TGAGGAGACGGTGACTGAGGT-3'

CD8 Hinge-F:
                                      (SEQ ID NO: 37)
5'-AGTCACCGTCTCCTCAACCACGACGCCAGCGCC-3'
```

-continued

CD8 Hinge-R:
(SEQ ID NO: 38)
5'-GTAGATATCACAGGCGAAGTCCA-3'

CD8 Transmembrane-F:
(SEQ ID NO: 39)
5'-CGCCTGTGATATCTACATCTGGGCGCCCTTGGC-3'

CD8 Transmembrane-R:
(SEQ ID NO: 40)
5'-TCTTTCTGCCCCGTTTGCAGTAAAGGGTGATAACCAGTG-3'

CD137-F:
(SEQ ID NO: 41)
5'-AAACGGGGCAGAAAGAAACTC-3'

CD137-R:
(SEQ ID NO: 42)
5'-TGCTGAACTTCACTCTCAGTTCACATCCTCCTTCTTCTTC-3'

TCR-F:
(SEQ ID NO: 43)
5'-AGAGTGAAGTTCAGCAGGAGCG-3'

TCR-R:
(SEQ ID NO: 44)
5'-GGAGAGGGGCGTCGACTTAGCGAGGGGGCAGGGC-3'

IRES-F:
(SEQ ID NO: 45)
5'-GCCCTGCCCCCTCGCTAAGCCCCTCTCCCTCCCC-3'

IRES-R:
(SEQ ID NO: 46)
5'-CCAGGGAGAAGGCAACTGGACCGAAGGCGCTTGTGGAGAAGGAGTTC
ATGGTGGCATTATCATCGTGTTTTTCAAAGGA-3'

IL6Rs1-F:
(SEQ ID NO: 47)
5'-GTTGCCTTCTCCCTGGGGCTGCTCCTGGTGTTGCCTGCTGCCTTCCC
TGCCCCAGACATCCAGATGACCCAGAG-3'

IL6Rs1-R:
(SEQ ID NO: 48)
5'-GCAGCTTTTCGGTTCTGAGGAGACTGTGACGAGGCT-3'

IL6Rs2-F:
(SEQ ID NO: 49)
5'-GTTGCCTTCTCCCTGGGGCTGCTCCTGGTGTTGCCTGCTGCCTTCCC
TGCCCCAGAAATTGTGATGACCCAGAG-3'

IL6Rs2-R:
(SEQ ID NO: 50)
5'-GCAGCTTTTCGGTTCGCTGCTCACGGTCACGGTGGT-3'

IL6Rs3-F:
(SEQ ID NO: 51)
5'-GTTGCCTTCTCCCTGGGGCTGCTCCTGGTGTTGCCTGCTGCCTTCCC
TGCCCCAGATATTCAGATGACCCAGAG-3'

IL6Rs3-R:
(SEQ ID NO: 52)
5'-GCAGCTTTTCGGTTCGCTGCTCACGGTCACGGTGGT-3' s0-F:
(SEQ ID NO: 53)
5'-GTTGCCTTCTCCCTGGGGCTGCTCCTGGTGTTGCCTGCTGCCTTCCC
TGCCCCATTGTTCTGGATTCCTGCTTCCA-3' s0-R:
(SEQ ID NO: 54)
5'-GCAGCTTTTCGGTTCTGCAGAGACAGAGACCAGAGT-3'

Fc-F:
(SEQ ID NO: 55)
5'-GAACCGAAAAGCTGCGATAAAAC-3'

-continued

Fc-R:
(SEQ ID NO: 56)
5'-CTAGCAATCTAGAGGTTATTTGCCCGGGCTCAGGCTCA-3'

WPRE-QPCR-F:
(SEQ ID NO: 57)
5'-CCTTTCCGGGACTTTCGCTTT-3'

WPRE-QPCR-R:
(SEQ ID NO: 58)
5'-GCAGAATCCAGGTGGCAACA-3'

Actin-QPCR-F:
(SEQ ID NO: 59)
5'-CATGTACGTTGCTATCCAGGC-3'

Actin-QPCR-R:
(SEQ ID NO: 60)
5'-CTCCTTAATGTCACGCACGAT-3'

CAR-QPCR-F:
(SEQ ID NO: 61)
5'-GACTTGTGGGGTCCTTCTCCT-3'

CAR-QPCR-R:
(SEQ ID NO: 62)
5'-GCAGCTACAGCCATCTTCCTC-3'

IL6-QPCR-F:
(SEQ ID NO: 63)
5'-GGATTCAATGAGGAGACTT-3'

IL6-QPCR-R:
(SEQ ID NO: 64)
5'-ATCTGTTCTGGAGGTACT-3'

CRP-QPCR-F:
(SEQ ID NO: 65)
5'-GACATTGGAAATGTGAACATGT-3'

CRP-QPCR-R:
(SEQ ID NO: 66)
5'-CACAGCTGGGGTTTGGTGA-3'

Fc-QPCR-F:
(SEQ ID NO: 67)
5'-GACATTGGAAATGTGAACATGT-3'

Fc-QPCR-R:
(SEQ ID NO: 68)
5'-CACAGCTGGGGTTTGGTGA-3'

3. The DNA sequences shown in SEQ ID NO: 12-SEQ ID NO: 68 were synthesized by Shanghai Generay Biotech Co., Ltd., and stored as oligonucleotide dry powder or plasmid;

4. Tool enzymes Nde I, Hpa I, Pvu II, Sac II, ApaL I, BamH I, Kpn I, Cla I and T4 DNA ligases were purchased from NEB;

5. PrimerSTAR HS DNA Polymerase, RN were purchased from Takara;

6. 0.22 μm-0.8 μm PES filters were purchased from millipore;

7. The Plasmid Extraction Kit and Agarose Gel Recovery Kit were purchased from MN;

8. TOP 10 Competent Cell were purchased from tiangen;

9. NaCl, KCl, $Na_2HPO_4.12H_2O$, $KH_2PO_4$, Trypsin, EDTA, $CaCl_2$), NaOH, PEG6000 were purchased from Shanghai Sangon Biotech;

10. Opti-MEM, FBS, DMEM, 1640, Pen-Srep, Hepes were purchased from invitrogen;

11. Biotinylated protein L and proteinG-HRP were purchased from GeneScript;

12. HRP-labeled secondary antibodies and DAB working fluid were purchased from ZSGB-BIO;

13. ECL+Plus™ Western blotting system purchased from Amersham;

13. ECL+Plus™ Western blotting system was purchased from Amersham;

14. DNeasy kit was purchased from Shanghai Generay Biotech Co., Ltd.;

15. Lymphocyte Separation Medium were purchased from Dakewe Biotech Co., Ltd.;

16. Phycoerythrin(PE)-conjugated streptavidin was purchased from BD Bioscience;

17. SA-HRP, TMB Substrate and ELISA Stop Solution were purchased from Yeasen Biotech Co., Ltd.;

18. *Mycoplasma* Detection Kit, Endotoxin Detection Kit, CD19$^+$-K562 cells and BCMA-IL6R-K562 cells were purchased from Shiao (Shanghai) Biotech Co., Ltd.;

19. LDH Detection Kit was purchased from promega.

II. Preparation Method of Recombinant Lentiviral Vectors 1vCAR19-IL6RscFv1, 1vCAR19-IL6RscFv2, 1vCAR19-IL6RscFv3, 1vCAR19-scFv0

Figure 3:
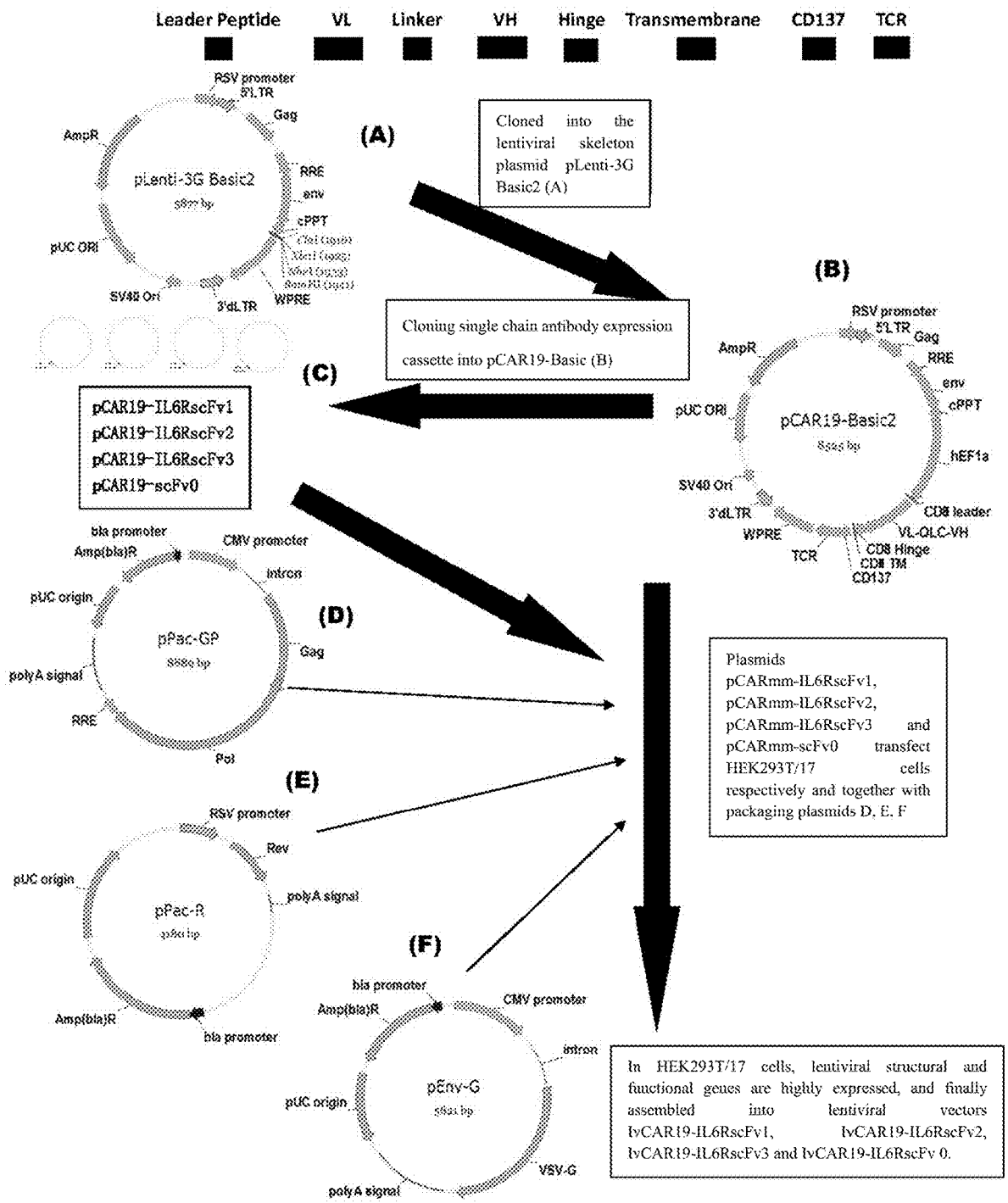
FIG. 3 is a flow chart for constructing the recombinant lentivirus vector in embodiment I of the invention; where part (A) is the structure diagram of the lentivirus skeleton plasmid pLenti-3G Basic2; part (B) is the structure diagram of the pCAR19-Basic2 plasmid; part (C) is the structure diagram of the pCAR19-IL6RscFv1, pCAR19-IL6RscFv2, pCAR19-IL6RscFv3 and pCAR19-scFv0 plasmid; part (D) is the structure diagram of the lentivirus packaging plasmid pPac-GP; part (E) is the structure diagram of the lentivirus packaging plasmid pPac-R; and part (F) is the structure diagram of membrane protein pEnv-G.

See FIG. 3. The preparation method of the recombinant lentiviral vector described in the invention is as follows:

1. The human EF1α promoters, CD8 leader chimeric receptor signal peptide, CD19 single chain antibody light chain VL, Optimal Linker C, CD19 single chain antibody heavy chain VH, CD8 chimeric receptor hinge, CD8 transmembrane transmembrane domain chimeric receptor, the chimeric receptor co-stimulation factor-CD137, TCR and T cell activation domain chimeric receptor fragments were cloned into the lentiviral cytoskeleton plasmid pLenti-3G Basic2 to obtain recombinant lentiviral plasmid pCAR19-Basic2, and the siRNA fragments were connected into pCAR19-Basic2 respectively to obtain IL-6 know-down recombinant lentiviral plasmids pCAR19-IL6RscFv1, pCAR19-IL6RscFv2, pCAR19-IL6RscFv3 and control pCAR19-scFv0.

Figure 4A:
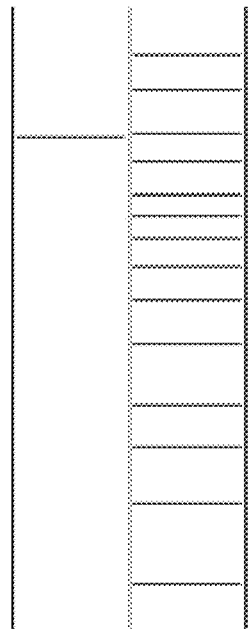
FIGS. 4A and 4B are enzyme digestion prediction and enzyme digestion agarose gel electrophoresis diagrams of the lentivirus skeleton plasmid pLenti-3G Basic2 in the embodiment 1 of the invention; where
Figure 4B:
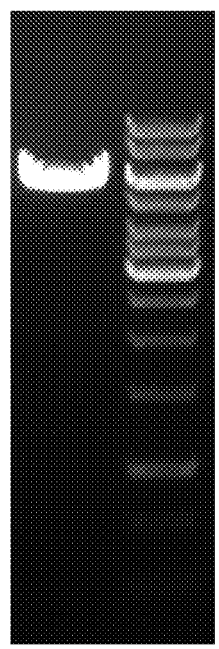

(1) The lentiviral cytoskeleton plasmid pLenti-3G Basic2 was double digested with Cla I and BamH I restriction enzymes. The product was electrophoresed on a 1.5% agarose gel to confirm the 5854 bp fragment V1 (see FIGS. 4A and 4B), then such gel was recovered and placed in an Eppendorf tube. The corresponding fragments were recovered with Agarose Gel Recovery Kit of MN (see Table 1), and the purity and concentration of the product were determined.

TABLE 1

| Procedures for the recovery of agarose gels | |
|---|---|
| 1. Sol | Add the sol solution in a ratio of 200 μl NTI/100 mg gel, and place it in a 50° C. water bath for 5-10 minutes. |
| 7. Bind to DNA | Centrifuge at 11,000 g for 30 seconds, and discard the filtrate. |
| 8. Wash membrane | Add 700 μl NT3, centrifuge at 11,000 g for 30 seconds, and discard the filtrate |
| 9. Wash membrane | Repeat the third step once |
| 10. Dry | Centrifuge at 11,000 g for 1 minute, replace with a new collection tube, and leave it at room temperature for 1 minute. |
| 11. Elute DNA | Add 15-30 μl NE, leave it at room temperature for 1 minute, centrifuge at 11,000 g for 1 minute, and then collect the filtrate. |

(2) Use the primers EF1α-F and EF1α-R with the synthesized SEQ ID NO: 12 as a template, and apply the system in Table 2. PCR circulation condition was: 98° C. 3 min, (98° C. 10 sec, 55° C. 15 sec, 72° C. 2 min)*35 cycle, 72° C. 10 min. The product was electrophoresed on a 1.5% agarose gel to confirm the 1208 bp fragment a, then such gel was recovered and placed in an Eppendorf tube. The corresponding fragments were recovered with Agarose Gel Recovery Kit of MN (see Table 1), and the purity and concentration of the product were determined.

TABLE 2

| 50 μl PCR reaction system | |
|---|---|
| Reagent | Volume (μl) |
| H$_2$O | 32.5 |
| 5 × Buffer (with Mg2+) | 10 |
| dNTP (2.5 mM each) | 4 |
| Primer1 (+)(10 μM) | 1 |
| Primer2 (−)(10 μM) | 1 |
| Template | 1 |
| PrimeSTAR | 0.5 |

(3) Use the primers CD8 leader-F and CD8 leader-R with the synthesized SEQ ID NO: 13 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 101 bp fragment b, then such gel was recovered and placed in an Eppendorf tube. The corresponding fragments were recovered with Agarose Gel Recovery Kit of MN (see Table 1), and the purity and concentration of the product were determined.

(4) Use the primers VL-F and VL-R with the synthesized SEQ ID NO: 14 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 336 bp fragment c, then such gel was recovered and placed in an Eppendorf tube. The corresponding fragments were recovered with Agarose Gel Recovery Kit of MN (see Table 1), and the purity and concentration of the product were determined.

(5) Use the primers OLC-VH-F and VH-R with the synthesized SEQ ID NO: 16 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 421 bp fragment d, then such gel was recovered and placed in an Eppendorf tube. The corresponding fragments were recovered with Agarose Gel Recovery Kit of MN (see Table 1), and the purity and concentration of the product were determined.

(6) Use the primers CD8 Hinge-F and CD8 Hinge-R with the synthesized SEQ ID NO: 17 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 147 bp fragment e, then such gel was recovered and placed in an Eppendorf tube. The corresponding fragments were recovered with Agarose Gel Recovery Kit of MN (see Table 1), and the purity and concentration of the product were determined.

(7) Use the primers CD8 Transmembrane-F and CD8 Transmembrane-R with the synthesized SEQ ID NO: 18 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 100 bp fragment f, then such gel was recovered and placed in an Eppendorf tube. The corresponding fragments were recovered with Agarose Gel Recovery Kit of MN (see Table 1), and the purity and concentration of the product were determined.

(8) Use the primers CD137-F and CD137-R with the synthesized SEQ ID NO: 19 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 142 bp fragment g, then such gel was recovered and placed in an Eppendorf tube. The corresponding fragments were recovered with Agarose Gel Recovery Kit of MN (see Table 1), and the purity and concentration of the product were determined.

(9) Use the primers TCR-F and TCR-R with the synthesized SEQ ID NO: 20 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 335 bp fragment h, then such gel was recovered and placed in an Eppendorf tube. The corresponding fragments were recovered with Agarose Gel Recovery Kit of MN (see Table 1), and the purity and concentration of the product were determined.

(10) Applying the system in Table 3, 1 μl each of DNA fragments b, c and d were taken as templates to add to Eppendorf tubes except for primers. PCR circulation condition was: 98° C. 3 min, (98° C. 10 sec, 60° C. 10 sec, 72° C. 30 sec)*6 cycle. To add primer CD8 leader-F/VH-R with the conditions as (98° C. 10 sec, 60° C. 10 sec, 72° C. 40 sec)*24 cycle, 72° C. 5 min. The product was electrophoresed on a 1.5% agarose gel to confirm the 814 bp fragment i, then such gel was recovered and placed in an Eppendorf tube. The corresponding fragments were recovered with Agarose Gel Recovery Kit of MN (see Table 1), and the purity and concentration of the product were determined.

TABLE 3

| 50 μl overlapping PCR reaction system | |
|---|---|
| Reagent | Volume (μl) |
| H₂O | 33.5-1* number of templates |
| 5 × Buffer (with Mg2+) | 10 |
| dNTP (2.5 mM each) | 4 |
| Primer1(+) (10 μM) | 1 |
| Primer2(−) (10 μM) | 1 |
| Template | 1* number of templates |
| PrimeSTAR | 0.5 |

(11) Applying the system in Table 3, 1 μl each of DNA fragments e, f, g and h were taken as templates to add to Eppendorf tubes except for primers. PCR circulation condition was: 98° C. 3 min, (98° C. 10 sec, 60° C. 10 sec, 72° C. 30 sec)*6 cycle. To add primer CD8 Hinge-F/TCR-R with the conditions as (98° C. 10 sec, 60° C. 10 sec, 72° C. 30 sec)*24 cycle, 72° C. 5 min. The product was electrophoresed on a 1.5% agarose gel to confirm the 704 bp fragment j, then such gel was recovered and placed in an Eppendorf tube. The corresponding fragments were recovered with Agarose Gel Recovery Kit of MN (see Table 1), and the purity and concentration of the product were determined.

Figure 5A:
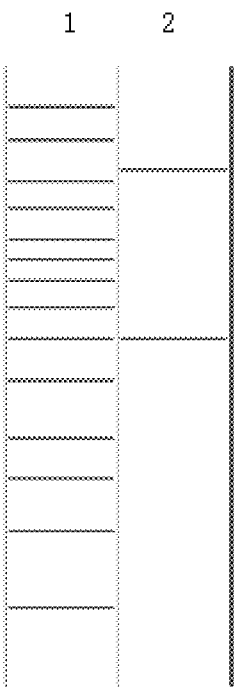
FIGS. 5A and 5B are enzyme digestion prediction and enzyme digestion agarose gel electrophoresis diagrams of recombinant lentiviral plasmid pCAR19-Basic2 in embodiment 1 of the invention; where
Figure 5B:
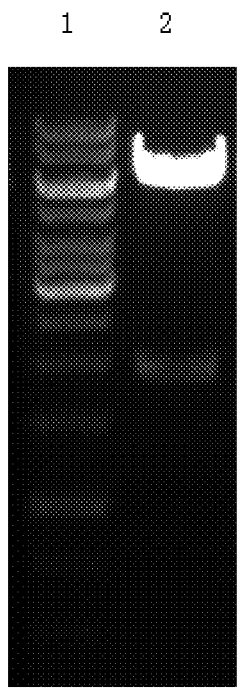
Figure 6A:
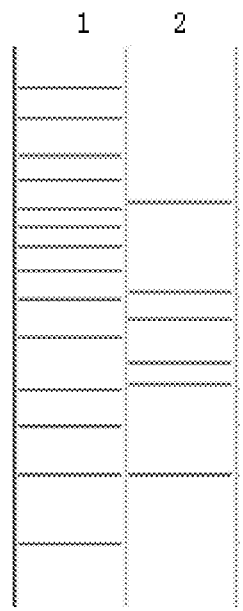
FIGS. 6A-6H are enzyme digestion prediction and enzyme digestion agarose gel electrophoresis diagrams of recombinant lentiviral vectors pCAR19-IL6RscFv1, pCAR19-IL6RscFv2, and pCAR19-IL6RscFv3 in the embodiment 1 of the invention; where
Figure 6B:
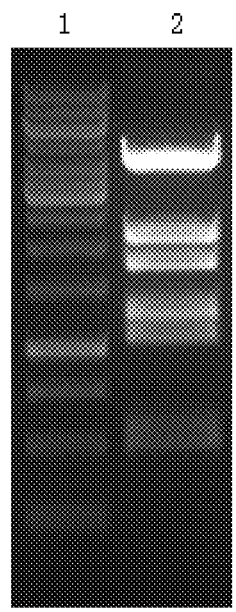
Figure 6C:
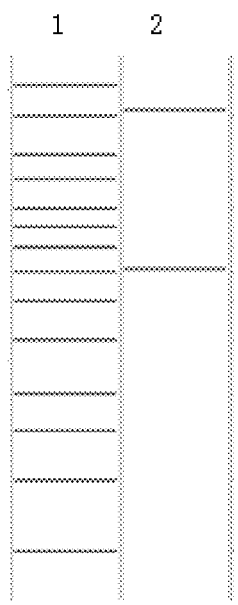
Figure 6D:
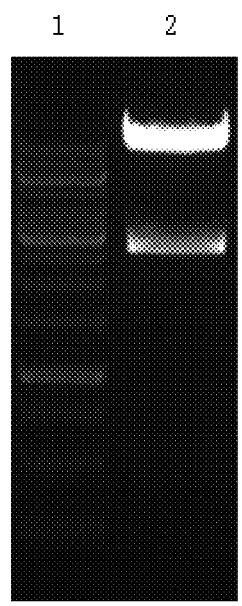
Figure 6E:
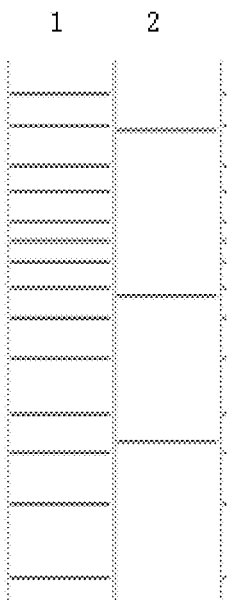
Figure 6F:
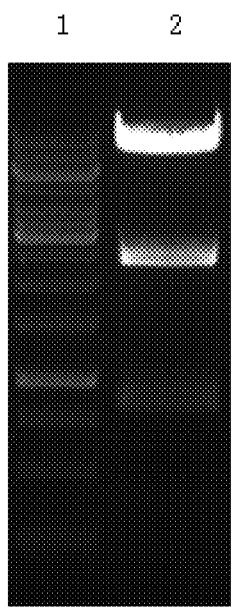
Figure 6G:
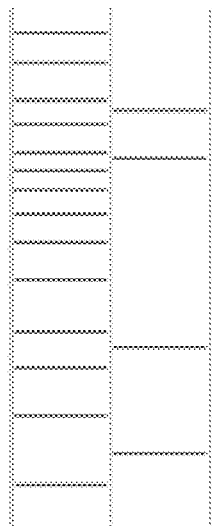
Figure 6H:
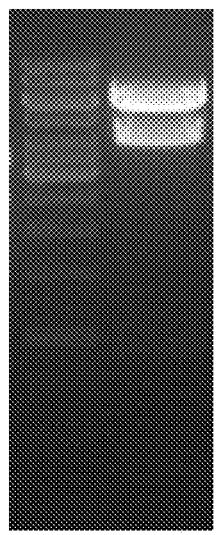

(12) The DNA fragments V1, a, i, j were added to the Eppendorf tubes in a total volume of 5 μl with a molar ratio of 1:1:1:1. 15 μl of the homologous recombinase reaction solution was added to the tubes, and the mixtures were incubated at 42° C. for 30 minutes. Place them on ice for 2-3 minutes. Add the reaction solution to 50 μl of TOP10, gently rotate to mix the contents, place them on ice for 30 minutes, then put the tubes in the thermostatic water bath pre-warmed to 42° C. for 90 seconds, and quickly transfer the tubes in an ice bath. The cells were allowed to cool for 2-3 minutes. Add 900 μl of LB medium to each tube, then put the tubes to a 37° C. shaker and incubate for 1 hour to resuscitate the bacteria. Take 100 μl of transformant bacteria solution to apply to an Amp LB agar plate, invert the plate, and culture in a thermostatic incubator at 37° C. for 16 hours. The clones were picked for colony PCR identification, and the correct clones were identified as recombinant lentiviral plasmid pCAR19-Basic2. Enzyme digestion identification was performed for the correct clones (see FIGS. 5A and 5B).

(13) The recombinant lentiviral plasmid pCAR19-Basic2 was double digested with Sal I and Nhe I restriction enzymes. The product was electrophoresed on a 1.5% agarose gel to confirm the 8491 bp fragment V2, then such gel was recovered and placed in an Eppendorf tube. The corresponding fragments were recovered with Agarose Gel Recovery Kit of MN (see Table 1), and the purity and concentration of the product were determined.

(14) The primers IRES-F and IRES-R were used to synthesize SEQ ID NO: 25 as templates. Using the system in Table 2, the conditions of PCR cycle were 98° C. 3 min, (98° C. 10 sec, 55° C. 15 sec, 72° C. 2 min)*35 cycle and 72° C. 10 min. The product was by agarose gel electrophoresis of 1.5%, and the fragment k of 605 bp was confirmed. The tapping gel was recovered in Eppendorf tube, and the corresponding fragments were recovered by agarose gel recovery kit of MN company (see Table 1), and the purity and concentration of the product were determined.

(15) The primers IL6Rs1-F and IL6Rs1-R were used to synthesize SEQ ID NO: 21 as templates. Using the system in Table 2, the conditions of PCR cycle were 98° C. 3 min, (98° C. 10 sec, 55° C. 15 sec, 72° C. 2 min)*35 cycle and 72° C. 10 min. The product was by agarose gel electrophoresis of 1.5%, and the fragment 1 of 754 bp was confirmed. The tapping gel was recovered in Eppendorf tube, and the corresponding fragments were recovered by agarose gel recovery kit of MN company (see Table 1), and the purity and concentration of the product were determined.

(16) The primers IL6Rs2-F and IL6Rs2-R were used to synthesize SEQ ID NO: 22 as templates. Using the system in Table 2, the conditions of PCR cycle were 98° C. 3 min, (98° C. 10 sec, 55° C. 15 sec, 72° C. 2 min)*35 cycle and 72° C. 10 min. The product was by agarose gel electrophoresis of 1.5%, and the fragment m of 777 bp was confirmed. The tapping gel was recovered in Eppendorf tube, and the corresponding fragments were recovered by agarose gel recovery kit of MN company (see Table 1), and the purity and concentration of the product were determined.

(17) The primers IL6Rs3-F and IL6Rs3-R were used to synthesize SEQ ID NO: 23 as templates. Using the system in Table 2, the conditions of PCR cycle were 98° C. 3 min, (98° C. 10 sec, 55° C. 15 sec, 72° C. 2 min)*35 cycle and 72° C. 10 min. The product was by agarose gel electrophoresis of 1.5%, and the fragment n of 774 bp was confirmed. The tapping gel was recovered in Eppendorf tube, and the corresponding fragments were recovered by agarose gel recovery kit of MN company (see Table 1), and the purity and concentration of the product were determined.

(18) The primers s0-F and s0-R were used to synthesize SEQ ID NO: 24 as templates. Using the system in Table 2, the conditions of PCR cycle were 98° C. 3 min, (98° C. 10 sec, 55° C. 15 sec, 72° C. 2 min)*35 cycle and 72° C. 10 min. The product was by agarose gel electrophoresis of 1.5%, and the fragment o of 729 bp was confirmed. The tapping gel was recovered in Eppendorf tube, and the corresponding fragments were recovered by agarose gel recovery kit of MN company (see Table 1), and the purity and concentration of the product were determined.

(19) The primers Fc-F and Fc-R were used to synthesize SEQ ID NO: 27 as templates. Using the system in Table 2, the conditions of PCR cycle were 98° C. 3 min, (98° C. 10 sec, 55° C. 15 sec, 72° C. 2 min)*35 cycle and 72° C. 10 min. The product was by agarose gel electrophoresis of 1.5%, and the fragment p of 726 bp was confirmed. The tapping gel was recovered in Eppendorf tube, and the corresponding fragments were recovered by agarose gel recovery kit of MN company (see Table 1), and the purity and concentration of the product were determined.

(20) DNA fragments (V2, k, l, p), (V2, k, m, p), (V2, k, n, p), (V2, k, o, p) were added into the Eppendorf tube with a total volume of 5 µl and at a molar ratio of 1:1:1 respectively, and 15 µl homologous recombinant enzyme reaction solution. After evenly mixed, they were incubated at 42° C. for 30 minutes and transferred to ice for 2-3 minutes. The reaction solution was added to 50 µl TOP10 and rotated gently to evenly mix the content. Place the tube in ice for 30 minutes, and heatly shock the tube for 90 seconds in a constant temperature water bath pot preheated to 42° C., quickly transfer the tube to the ice bath, cool the cells for 2-3 minutes, add 900 µl LB culture medium to each tube, then transfer the tube to a shaking bed at 37° C., incubate for 1 hour to resuscitate the bacteria, take 100 µl transformed bacteria solution and coat it on Amp LB agar plate, invert the flat dish, and put it in a constant temperature incubator at 37° C., and culture for 16 hours. The correct clones were identified by colony PCR as recombinant lentivirus plasmids pCAR19-IL6RscFv1, pCAR19-IL6RscFv2, pCAR19-IL6RscFv3 and control pCAR19-scFv0. The correct clone would be identified with enzyme digestion (see FIGS. 6A-6H).

2. Packaging of 1vCAR19-IL6RscFv1, 1vCAR19-IL6RscFv2, 1vCAR19-IL6RscFv3, 1vCAR19-scFv0

(1) Complete medium: take out the pre-warmed fresh medium, add 10% FBS+5 ml Pen-Srep, and mix them upside down.

(2) 1×PBS solution: weigh 8 g of NaCl, 0.2 g of KCl, 3.58 g of $Na_2HPO_4.12H_2O$, 0.24 g of $KH_2PO_4$, and put them in a 1000 ml beaker, and add 900 ml of Milli-Q grade ultrapure water to dissolve. After completion of the dissolution, the volume was adjusted to 1000 ml using a 1000 ml measuring cylinder, and the mixture was sterilized by heat sterilization at 121° C. for 20 minutes.

(3) 0.25% Trypsin solution: weigh 2.5 g of Trypsin, 0.19729 g EDTA, and put them in a 1000 ml beaker, and add 900 ml of 1×PBS solution to dissolve. After completion of the dissolution, the volume was adjusted to 1000 ml using a 1000 ml measuring cylinder, and the mixture was sterilized via 0.22 M filter. It could be saved in the refrigerator at −20° C. for long-term use.

(4) 0.5M $CaCl_2$ solution: weigh 36.75 g of $CaCl_2$, and dissolve it with 400 ml of Milli-Q grade ultrapure water; The volume was adjusted to 500 ml with Milli-Q grade ultrapure water, and mixed; The mixture was sterilized via 0.22 M filter, and stored in 50 ml centrifuge tubes with about 45 ml in each tube at 4° C.

(5) 2×HBS solution: weigh 4.09 g of NaCl, 0.269 g of $Na_2HPO4$, 5.96 g of Hepes, and dissolve them with 400 ml Milli-Q grade ultrapure water; After calibrating the PH meter, the PH of the HBS solution was adjusted to 7.05 with 2M NaOH solution. It was about 3 ml of 2M NaOH to consume to adjust the PH of each bottle of HBS.

(6) The frozen HEK293T/17 cells were removed from the liquid nitrogen container and rapidly transferred to a 37° C. water bath for 1-2 minutes, and then put them on a super clean bench. Aseptically transfer all the liquid in the freezing tube to a 10 $cm^2$ petri dish, and make up DMEM containing 10% FBS to 8 mL/10 $cm^2$ dish, and observe the cells under microscope after 24 hours. Passage was performed with the degree of cell confluence greater than 80%.

(7) HEK293T/17 cells with good cell status and no pollution were selected, and each 2-6 petri dishes were used as a group. After trypsinizing the cells, 4-12 ml of complete medium was pipetted with an electric pipette to add 2 ml to each digested dish to avoid drying the dish; All cells were isolated into single cell suspensions using a 1 ml pipette and transferred to medium bottles.

(8) The remaining cells in the above 2-6 petri dishes were transferred to the medium bottles, and the petri dishes were rinsed with the medium again.

(9) Close the cap of the medium bottles and turn them upside down for about 10 times to fully mixed the cell suspension. Transfer the cells to 8-24 10 $cm^2$ petri dishes. For each dish, there shall be about $4 \times 10^6$ cells/10 ml complete medium. If the cell density is significantly different from the expected, the number of cells is required to be counted, and then the cells will be inoculated according to the quantity of $4 \times 10^6$ per dish.

(10) Arrange each of the 6 petri dishes into a pile, and keep the fit between the upper and lower dishes. Shake the petri dishes left and right, back and forth several times to make cells fully spread out, and then put them into an incubator with 5% $CO_2$. The remaining cells were treated as the same.

(11) Upon Checking the passage cells, the cells shall be at 70-80% confluence, with full contour, good attachment and even distribution in petri dishes.

(12) For changing the solution, the medium was replaced with fresh complete medium with 9 ml per dish. The $CO_2$ concentration of incubator was increased to 8%.

(13) To prepare $DNA/CaCl_2$) according to N+0.5. The amount of HEK293T/17 cell transfection plasmid per dish was used in the following ratios: recombinant lentiviral plasmid (20 µg), pPac-GP (15 µg), pPac-R (10 g), pEnv-G (7.5 µg). Take a new 5 ml centrifuge tube, add 0.5M CaCl2: 0.25 ml, recombinant lentiviral plasmid 20 µg: pPac-GP 15 g: pPac-R 10 g: pEnv-G 7.5 µg, supplement ultrapure water to 0.5 ml, and cover the cap to mix them fully.

(14) Take another 5 ml centrifuge tube and add 0.5 ml DNA/CaCl2 solution. Open a vortex mixer, hold the upper end of the 5 ml centrifuge tube with one hand, and make the bottom of the tube contact the oscillation chamber, so that the liquid could spread on the tube wall. Take a 1 ml pipette with anther hand to suck 0.5 mL 2×HBS solution, add it into the centrifuge tube slowly and control the flow velocity. It was advisable to complete the drip in half a minute. After 2×HBS was added, it should be oscillated for another 5 seconds, and then stop oscillating. It could be directly added into the cells that need transfection.

(15) Take a dish of cells and drop 1 mL calcium transfection solution in the centrifuge tube in the dish to distribute the calcium transfection solution throughout the petri dish as much as possible.

(16) After the calcium transfection solution was added, the petri dish was marked on the cover, and put back in another incubator with 5% $CO_2$. Make sure that the petri dish was placed horizontally, and that there were no more than 6 petri dishes in each pile. These dishes were placed in the incubator with 5% $CO_2$ for 6-8 h.

(17) The $CO_2$ concentration of the first incubator was adjusted at 5%.

(18) The cells status was check 24 hours later. The cell confluence should be around 80-85% and in good condition. Aspirate the medium and replace 10 ml of fresh DMEM complete medium.

(19) The transfection efficiency was observed 48 hours later. Most cells were still adherent. It could be seen that more than 95% of the cells would have green fluorescence. The supernatant of the same virus packaging was collected together, and 10 mL of fresh medium was added to the petri dish.

(20) The same virus supernatant was collected again 72 hours later. The two collections were put together, and the petri dishes were discarded; the supernatant collected at this time contained the recombinant lentiviral vectors 1vCAR19-IL6RscFv1, 1vCAR19-IL6RscFv2, 1vCAR19-IL6RscFv3, 1vCAR19-scFv0.

Embodiment 2 Concentration and Detection of Recombinant Lentivirus Vector

Figure 7:
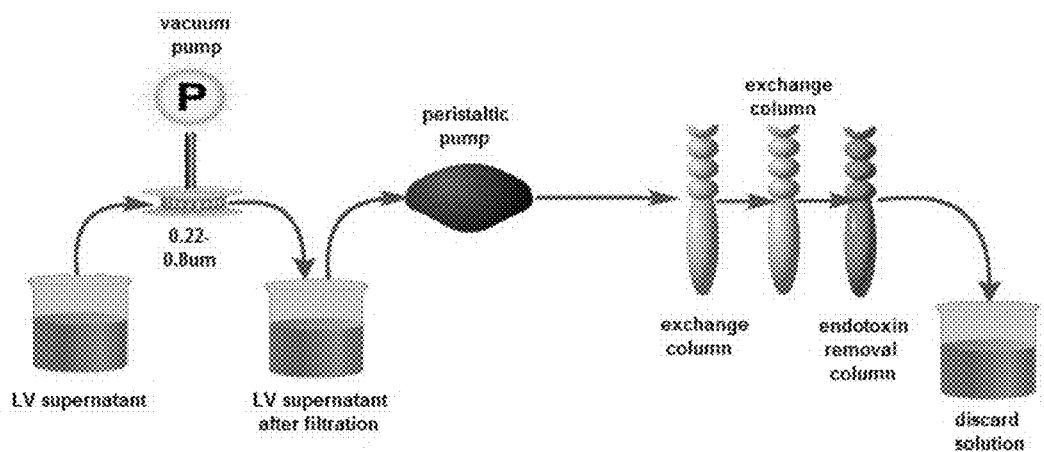
FIG. 7 is a flow chart of ion exchange chromatography for purification of recombinant lentivirus vector in embodiment 2 of the invention.

I. Purification of Recombinant Lentiviral Vectors by Ion Exchange Chromatography (see FIG. 7);

(1) The collected supernatant was filtered through a 0.22 m-0.8 m PES filter using a Thermo vacuum pump to remove impurities.

(2) 1.5M NaCl 250 mM Tris-HCl (PH6-8) was added to the supernatant at a ratio of 1:1 to 1:10.

(3) Two ion exchange columns were placed in series, and they were passed through sequentially by 4 ml 1M NaOH, 4 ml 1M NaCl, 5 ml 0.15M NaCl 25 mM Tris-HCl (pH 6-8) solution.

(4) The solution obtained in step 2 was pumped into the ion exchange column with a peristaltic pump at a rate of 1-10 ml/min.

(5) After all the supernatant was passed through the column, it was washed with 10 ml of 0.15M NaCl 25 mM Tris-HCl (pH 6-8) solution.

(6) According to the sample size, 1-5 ml of 1.5M NaCl 25 mM Tris-HCl (pH 6-8) was used for elution and the eluate was collected.

(7) The eluate was divided into tubes about 25 to 50 µl each, and stored in a refrigerator with −80° C. for long-term storage.

II. Titre Determination (1) 293T cells were inoculated with 24-well plates. The number of cells in each well was $5 \times 10^4$, and the volume of medium added was 500 ul. As the growth rate of different types of cells was different, the rate of cell fusion during viral infection was 40%-60%.

(2) Three sterile EP tubes were prepared, and 90 ul fresh complete medium (high glucose DMEM+10% FBS) was added into each tube to inoculate the cells. 24 hours later, the cells in the two pores were taken and counted with a hemocytometer to determine the actual number of cells at the time of infection, denoted as N.

(3) 10 ul of the virus stock to be determined was added to the first tube. After gently mixing, 10 ul of the virus stock was added to the second tube, and then sequentially operated until the last tube; 410 ul complete medium (high glucose DMEM+10% FBS) was added into each tube, and the final volume was 500 ul.

(4) 20 hours after the infection, the cultural supernatant was removed and replaced with 500 µl complete medium (high glucose DMEM+10% FBS). The cells was continuously cultured for 48 hours in 5% $CO_2$.

(5) After 72 hours, the fluorescence expression was observed. Under normal circumstances, the number of fluorescence cells decreased with the increase of dilution ratio. At the same time, photos were taken.

(6) The cells were digested with 0.2 ml 0.25% trypsin-EDTA solution, and then they were placed at 37° C. for 1 minute. The whole cellular surface were purged with medium, and the cells were collected by centrifugation. Genomic DNA was extracted according to the instructions of DNeasy kit. 200 µl of eluent were added to each sample tube to remove DNA, and then they were quantified.

(7) The DNA detection qPCRmix manifold I was prepared (QPCR primer sequences were SEQ ID NO: 57-SEQ ID NO: 58):

2×TaqMan Master Mix 25 µl×n
Forward primer (100 pmol ml−1) 0.1 µl×n
Reverse primer (100 pmol ml-1) 0.1 µl× n
Probe (100 pmol ml-1) 0.1 µl×n
$H_2O$ 19.7 µl×n n=number of reactions. For example, the total n were 40. 1 ml of 2×TaqMan Universal PCR Master Mix, 4 µl of forward primer, 4 µl of reverse primer, 4 µl of probe and 788 µl of $H_2O$ were mixed and Placed on ice after being shaken.

(8) The reference DNA detection qPCRmix manifold II were prepared (QPCR primer sequences were SEQ ID NO: 59-SEQ ID NO: 60):

2×TaqMan Master Mix 25 µl×n
10×RNaseP primer/probe mix 2.5 µl×n
$H_2O$ 17.5 µl×n n=number of reactions. For example, the total n were 40. 1 ml of 2×TaqMan Universal PCR Master Mix, 100 µl pf 10×RNaseP primer/probe mix and 700 µl of $H_2O$ were mixed and placed on ice after being shaken.

(9) The PCR system was established on a pre-cooled 96-well PCR plate. Take 45 µl from each tube of manifold I to add to the wells of each row of A-D. Take 45 µl from each tube of manifold II to add to the wells of each row of E-G.

(10) 5 µl of the standard plasmid and the genomic DNA from the samples to be tested were taken respectively to add to the A-D row, and each sample was repeated once. 1 well was left to add 5 µl of water as no-template control.

(11) 5 µl of the genomic standards and the genomic DNA from the samples to be tested were taken respectively to add to the E-G row, and each sample was repeated once. 1 well was left to add 5 µl of water as no-template control.

(12) The quantitative PCR instrument used was the ABI PRISM 7500 quantitative system. The cyclic conditions were set to: 50° C. 2 min, 95° C. 10 min, (95° C. 15 sec, 60° C. Imin)×40 cycle.

Data analysis: the copy number of lentiviral vectors integrated in the measured DNA samples was calibrated with the number of genomes to obtain the copy number of viruses integrated in each genome.

The calculation formula of integration units per ml (IU $ml^{-1}$) was as follows:

IU $ml^{-1}$=(C×N×D×1000)/V wherein: C=the average virus copy number per genome integration N=number of cells at the time of infection (approximately $1 \times 10^5$)

D=dilution of the viral vector

V=the volume of diluted virus added

Figure 8:
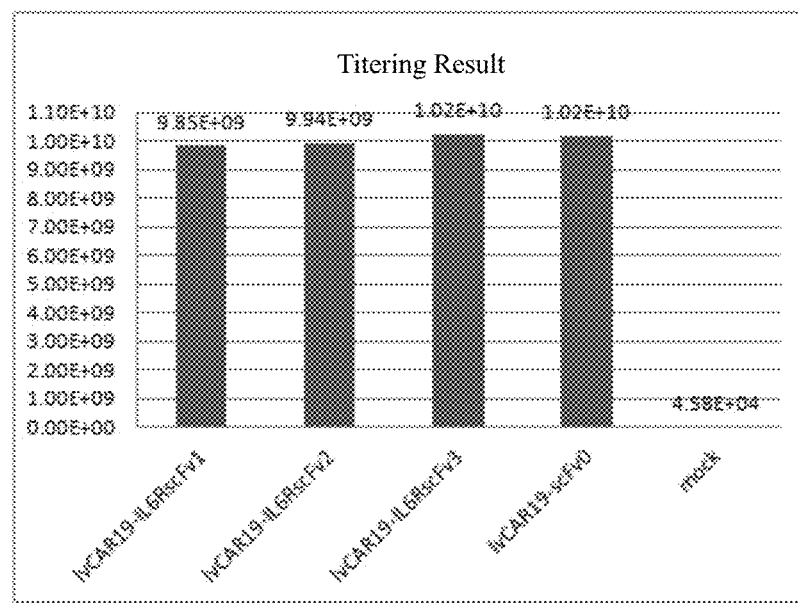
FIG. 8 is a schematic diagram of titer detection results of recombinant lentivirus vectors in embodiment 2 of the invention.

(13) Titer results of recombinant lentiviral vectors 1vCAR19-IL6RscFv1, 1vCAR19-IL6RscFv2, 1vCAR19-IL6RscFv3, 1vCAR19-scFv0 (see FIG. 8).

III. Endotoxin Determination (1) The working standard of endotoxin was 15 EU per dose.

(2) Sensitivity of Tachypiens Amebocyte Lysate (TAL) λ=0.25 EU/ml, 0.5 ml/tube.

(3) Dilution of endotoxin standard: take one endotoxin standard, dilute it into 4λ and 2λ solution with BET water, seal with sealing film and vortex for 15 min; During dilution, each dilution step should be mixed on the vertex mixer for 30 s.

(4) Adding: Several TAL were taken, each was dissolved in 0.5 ml of BET water, and then divided into several exdotoxin-free tubes (0.1 ml each tube). Two of them were negative control which were added 0.1 ml of BET water to each of them.

Two tubes were positive control which were added 0.1 ml of endotoxin working standard solution with concentration of 2λ to each of them.

Two tubes were positive control of sample which were added 0.1 ml sample solution contained 2λ endotoxin standard (1 ml of 20× dilution of sample to be tested+1 ml of solution contained 4λ endotoxin standard=2 ml of 40× dilution of sample contained 2λ endotoxin standard). Two tubes were positive control of sample which were added 0.1 ml sample solution contained 2λ endotoxin standard (1 ml of 20× dilution of sample to be tested+1 ml of solution contained 4λ endotoxin standard=2 ml of 40× dilution of sample contained 2λ endotoxin standard).

TABLE 5

Dilution ratio of exdotoxin and corresponding endotoxin content

| Dilution Multiple | Original Fluid | 5 | 10 | 20 | 40 | 80 | 160 |
|---|---|---|---|---|---|---|---|
| Corresponding EU/ml | 0.25 | 1.25 | 2.5 | 5 | 10 | 20 | 40 |
| Results | | | | | | | |

(5) The endotoxin detection results of the recombinant lentiviral vectors 1vCAR19-IL6RscFv1, 1vCAR19-IL6RscFv2, 1vCAR19-IL6RscFv3, 1vCAR19-scFv0 (as shown in Table 6) showed that the endotoxin content was between 0~2.5 EU/ml, which met the requirements.

TABLE 6

Detection results of endotoxin of recombinant lentiviral vectors

| | Dilution Multiple | | | | | | |
|---|---|---|---|---|---|---|---|
| | Original Fluid | 5 | 10 | 20 | 40 | 80 | 160 |
| | Corresponding EU/ml | | | | | | |
| | 0.25 | 1.25 | 2.5 | 5 | 10 | 20 | 40 |
| lvCAR19-1761 | (+) | (+) | (−) | (−) | (−) | (−) | (−) |
| lvCAR19-1762 | (+) | (+) | (+) | (−) | (−) | (−) | (−) |
| lvCAR19-1763 | (+) | (+) | (−) | (−) | (−) | (−) | (−) |
| lvCAR19-1764 | (+) | (+) | (−) | (−) | (−) | (−) | (−) |
| lvCAR19-1765 | (−) | (−) | (−) | (−) | (−) | (−) | (−) |
| lvCAR19-1766 | (+) | (−) | (−) | (−) | (−) | (−) | (−) |
| lvCAR19-1767 | (+) | (+) | (−) | (−) | (−) | (−) | (−) |
| lvCAR19-1768 | (+) | (+) | (−) | (−) | (−) | (−) | (−) |
| lvCAR19-1769 | (+) | (+) | (+) | (−) | (−) | (−) | (−) |

IV. Measurement and Comparison of *Mycoplasma*.

(1) Three days before the experiment, the cell samples were cultured in antibiotic-free medium.

(2) 1 ml cell suspension (more than 1*105 cells) was collected and placed in a 1.5 ml centrifugal tube.

(3) Centrifuge for 1 min, collect sediment and discard culture medium.

(4) Adding 500 ul PBS, blowing or whirlpool oscillation with the gun head, and resuspend sediment. Centrifugation for 5 min at 13000×g.

(5) Repeat step (4).

(6) Add 50 μl Cell Lysis Buffer, blow and suck with gunhead, mix well, and incubate in water bath at 55° C. for 20 minutes.

(7) The samples were heated at 95° C. for 5 minutes.

(8) After centrifugation for 5 min, 5 μl supernatant was used as template. The 25 μl PCR reaction system was ddH20 6.5 μl, Myco Mix 1 μl, 2× Taq Plus Mix Master (Dye Plus) 12.5 μl and template 55 μl. The cycle conditions of PCR were 95° C. 30 sec, (95° C. 30 sec, 56° C. 30 sec, 72° C. 30 sec)*30 cycle and 72° C. 5 min.

(9) *Mycoplasma* detection results (as shown in FIG. 9) showed that recombinant lentiviral vectors 1vCAR19-IL6RscFv1, 1vCAR19-IL6RscFv2, 1vCAR19-IL6RscFv3 and 1vCAR19-scFv0 did not contain *Mycoplasma*.

Embodiment 3 Functional Detection of Recombinant Lentiviral Vectors 1vCAR19-IL6RscFv1, 1vCAR19-IL6RscFv2, 1vCAR19-IL6RscFv3 and 1vCAR19-scFv0.

I. Detection of Cellular Level Expression of CAR Gene:

(1) After infection of PBMC cells by recombinant lentiviral vectors 1vCAR19-IL6RscFv1, 1vCAR19-IL6RscFv2, 1vCAR19-IL6RscFv3 and 1vCAR19-scFv0, and control virus Mock. RT-PCR was used to detect the mRNA transcriptional levels of CAR gene and scFv gene by collecting cells, and to verify the expression of CAR gene and scFv gene. If the mRNA transcriptional level of CAR gene and scFv gene increased, the expression of transcription level was successful.

(2) After infection of PBMC cells by recombinant lentiviral vectors 1vCAR19-IL6RscFv1, 1vCAR19-IL6RscFv2, 1vCAR19-IL6RscFv3 and 1vCAR19-scFv0, and control virus Mock. western blot was used to detect the expression level of CAR protein by collecting cells, and to verify the expression of CAR gene. If the expression level of CAR protein increased, the translation level of CAR gene was successfully expressed.

(3) After infection of PBMC cells by recombinant lentiviral vectors 1vCAR19-IL6RscFv1, 1vCAR19-IL6RscFv2, 1vCAR19-IL6RscFv3 and 1vCAR19-scFv0, and control virus Mock. The expression level of scFv protein was detected by ELISA in the supernatant of cultured cells to verify the expression of scFv gene. If the expression level of scFv protein increased, the translation level of scFv gene was successfully expressed.

(4) Infect cells with 1vCAR19-IL6RscFv1, 1vCAR19-IL6RscFv2, 1vCAR19-IL6RscFv3 and 1vCAR19-scFv0 of MOI=15 and control virus Mock, after 48 hours, extract the total RNA and total protein of cells from the 6 hole plate to carry out the quantitative fluorescence PCR and immunoblot experiment respectively. Specific steps: wrapping four holes of 6-hole plate, adding corresponding PBS and RN to each hole, and staying overnight at 4° C. After 12 hours, the virus was coated with MOI=15 and placed in incubator at 37° C. for 5 hours. The virus supernatant in the 6 hole plate was discarded and washed twice with PBS. PBMC was coated with 1*106/hole (separated from human blood with lymphocyte separating fluid). Add 500 ul culture medium (containing 10% serum, 20 U/ml IL-2, Polybrene 8 ug/ml) and place static for 20 minutes, centrifuge for 30 minutes at 1000 g 20° C. and culture for 48 hours at 37° C.

(5) Total RNA was extracted from PBMC cells in 6 hole plate by Trizol method. Reverse transcription was used to amplify the cDNA. Quantitative fluorescence PCR experiment was performed with CAR gene QPCR primers (SEQ ID NO: 61-SEQ ID NO: 62) and scFv gene QPCR primers (SEQ ID NO: 67-SEQ ID NO: 68). The reaction system was shown in Table 7. The internal reference Actin was used as the control group to verify the transcription of the mRNA.

TABLE 7

| 20 µl qPCR reaction system | |
|---|---|
| reagent | volume(µl) |
| SYBR premix ex taq: | 10 µl |
| ROX Reverse Dye (50x) | 0.4 µl |
| upstream primers (2.5 µM): | 0.5 µl |
| downstream primers (2.5 µM): | 0.5 µl |
| cDNA | 1.0 µl |
| ddH$_2$O | 7.6 µl |

(6) Western Blot was used to separate the total proteins extracted from PBMC in accordance with relative molecular mass by polyacrylamide gel electrophoresis. The protein was transferred to PVDF membrane by wet rotation (4° C., 400 mA, 120 min). PVDF membranes were sealed at room temperature for 1 hour with a sealing solution (TBST solution containing 5% skimmed milk), and Biotinylated protein L was diluted at 1:1000 with the sealing solution. Then they were incubated with the sealed PVDF membranes at room temperature for overnight at 4° C. TBST was washed three times, 10 minutes each time. The corresponding SA-HRP was diluted at 1:500, and PVDF membrane was incubated at room temperature for 2 hours, and TBST was washed three times, 10 minutes each time. Amersham company's ECL+plus TM Western blotting system kit was used for color rendering. X-ray development produces film showing strips.

(7) Enzyme Linked ImmunoSorbent Assay (ELISA) was used to coat the 1:2, 1:5 and 1:10 diluted supernatant of cell culture into 96 hole plate. Negative control, positive control and blank hole were set up at the same time and overnight at 4° C. Wash three times the next day, add fresh 1:10000 diluted proteinG-HRP 0.1 ml to the reaction pore, incubate at 37° C. for 30-60 minutes, wash, and wash with pure water for the last time. The TMB substrate solution added into the reaction pore was 0.1 ml and incubated at 37° C. for 10-30 minutes. ELISA reaction termination solution added into each reaction pore was 0.05 ml. OD values of each pore were measured at 405 nm on the enzyme label.

Figure 10B:
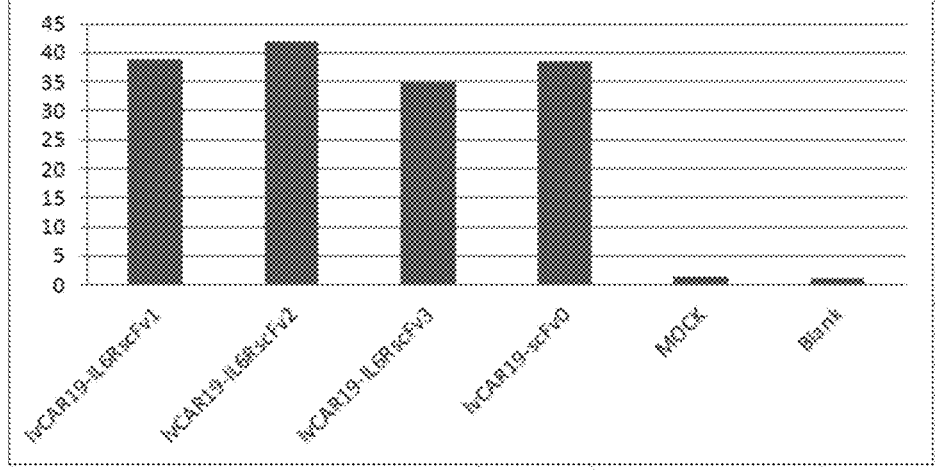

(8) RT-QPCR inspection showed that the transcription levels of CAR gene and scFv gene of recombinant lentivirus vector after infected with PBMC were significantly higher than those in empty cells (as shown in FIGS. 10A and 10B), indicating that the transcription levels of CAR gene and scFv gene were successfully expressed.

Figure 11A:
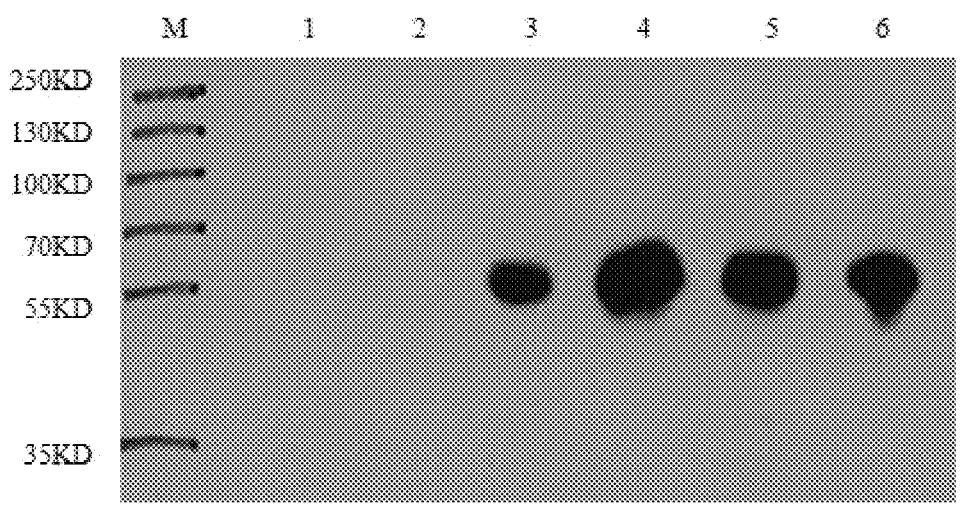
FIGS. 11A and 11B are WB detection diagrams of CAR protein expression in PBMC cells in embodiment 3 of the invention; where the results show that CAR protein is highly expressed in PBMC cells.
Figure 11B:
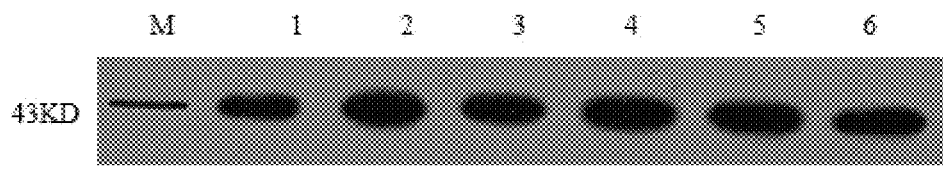

(9) Western Blot results showed that the expression level of CAR protein of recombinant lentivirus vector infected with PBMC was significantly higher than that of control virus MOCK and empty cells (as shown in FIGS. 11A and 11B), indicating that the translation level of CAR gene was successfully expressed.

Figure 12:
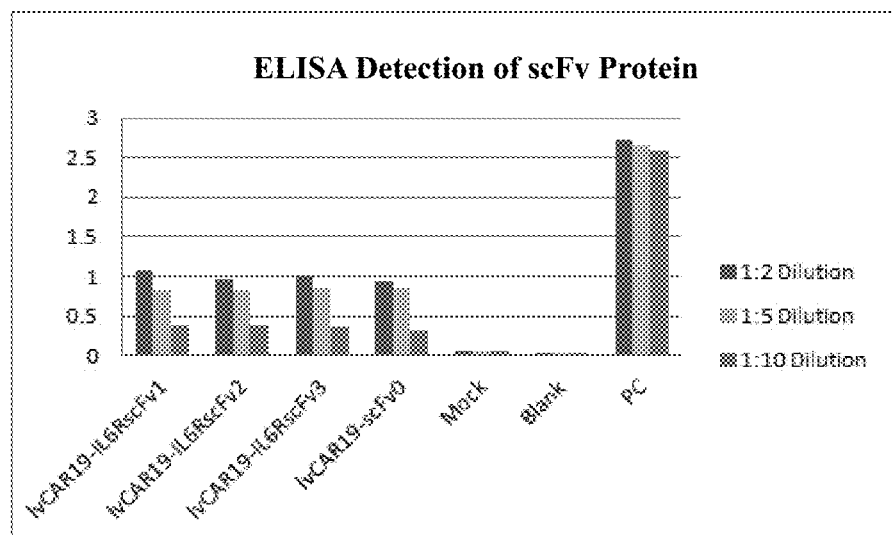
FIG. 12 is an ELISA test result of the expression of scFv protein in embodiment 3 of the invention. The results show that scFv protein is highly expressed in PBMC cells.

(10) Enzyme linked immunosorbent assay (ELISA) results showed that the expression level of scFv protein of recombinant lentivirus vector infected with PBMC was significantly higher than that of control virus MOCK and empty cells (as shown in FIG. 12), indicating that the translation level of scFv gene was successfully expressed.

II. Evaluation of Cytotoxicity Test (1) CD19+-K562 cells and PBMC cells were cultured respectively.

(2) Four days before the start of the experiment, culture virus infected PBMC cells of 1vCAR19-IL6RscFv1, 1vCAR19-IL6RscFv2, 1vCAR19-IL6RscFv3 and 1vCAR19-scFv0 of MOI=15 respectively for 72-96 h, then start to arrange the experiment.

(3) The target cells (CD19+-K562) 4×105 cells and effector cells (PBMC cells transduced by 1vCAR19-IL6RscFv1, 1vCAR19-IL6RscFv2, 1vCAR19-IL6RscFv3 and 1vCAR19-scFv0) 2.8×106 cells were collected. The cells were centrifuged at 800 g for 6 minutes and the supernatant was discarded.

(4) The target cells and effector cells were resuspended with 1 ml 1×PBS solution. The cells were centrifuged at 800 g for 6 minutes and the supernatant was discarded.

(5) Repeat step (3) for one time.

(6) 700 ul culture medium (1640 culture medium+10% FBS) was used to resuspend effector cells and 2 ml culture medium (1640 culture medium+10% FBS) was used to resuspend target cells.

(7) The experimental holes with effective target ratio of 1:1, 5:1 and 10:1 were set up, and the control group was set up with 3 compound holes in each group.

(8) 250×g, 5 min plate centrifugation.

(9) It was cultured in a 5% CO2 incubator at 37° C. for 24 hours.

(10) 250×g, 5 min plate centrifugation.

(11) The 50 ul supernatant of each hole was taken to the new 96 hole plate, and the 50 ul substrate solution was added to each hole (light avoidance operation).

(12) Breeding in dark for 25 minutes.

(13) 50 ul termination solution was added into each hole.

(14) 490 nm absorbance was measured by enzyme labeling.

(15) Average the three multiple holes; the average value of the absorbance values of all experimental holes, target cell holes and effector cell holes deducting the background absorbance values of the culture medium; the average value of the maximum absorbance values of target cells deducting the volume-corrected control absorbance values.

Figure 13:
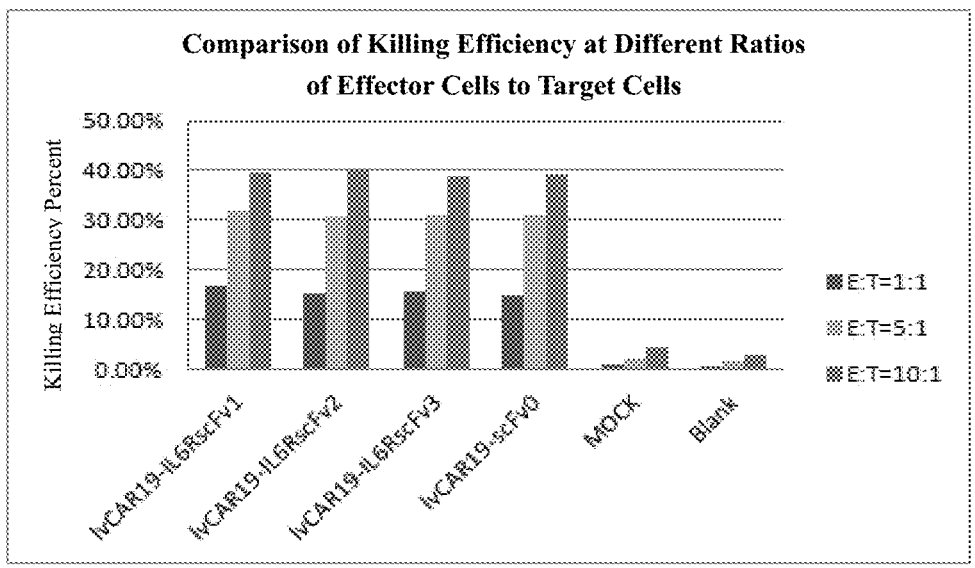
FIG. 13 is a schematic diagram of killing situation to the target cells after 24 h in co-culture of different effector cells with target cells in PBMC transduced by recombinant lentivirus vector of embodiment 3 of the invention.

(16) The corrected values obtained in step (15) are introduced into the following formula to calculate the percentage of cytotoxicity produced by each target-to-effect ratio. Results As shown in FIG. 13, the killing efficiency of PBMC cells transduced by 1vCAR19-IL6RscFv1, 1vCAR19-

IL6RscFv2, 1vCAR19-IL6RscFv3 and 1vCAR19-scFv0 recombinant lentiviral vectors was significantly higher than that of PBMC empty cells and control viruses under several effect-target ratios, indicating that the expression of scFv gene had little effect on the function of CAR gene.

Killing efficiency=(experimental hole–effector cell hole–target cell hole)/(maximum hole of target cell–target cell hole)×100%

III. Evaluation of Blocking Effect of IL-6R (mRNA transcription level of IL-6 and CRP).

(1) Culture CD19+-IL6R-K562 cells and PBMC cells respectively.

(2) Four days before the start of the experiment, culture virus infected PBMC cells of 1vCAR19-IL6RscFv1, 1vCAR19-IL6RscFv2, 1vCAR19-IL6RscFv3 and 1vCAR19-scFv0 of MOI=15 respectively for 72-96 h, then start to arrange the experiment.

(3) The target cells (CD19+-IL6R-K562) $4×10^5$ cells and effector cells (PBMC cells transduced by 1vCAR19-IL6RscFv1, 1vCAR19-IL6RscFv2, 1vCAR19-IL6RscFv3 and 1vCAR19-scFv0) $2.8×10^6$ cells were collected. The cells were centrifuged at 800 g for 6 minutes and the supernatant was discarded.

(4) The target cells and effector cells were resuspended with 1 ml 1×PBS solution. The cells were centrifuged at 800 g for 6 minutes and the supernatant was discarded.

(5) Repeat step (4) for one time.

(6) 700 ul culture medium (1640 culture medium+10% FBS) was used to resuspend effector cells and 2 ml culture medium (1640 culture medium+10% FBS) was used to resuspend target cells.

(7) The experimental holes with effective target ratio of 10:1 were set up, and the control group was set up.

(8) 250×g, 5 min plate centrifugation.

(9) Cultured in 5% CO2 incubator at 37° C. for 12 hours, centrifuged at 1000×g for 2 minutes, collect total mRNA from cells and reverse cDNA to detect IL-6 mRNA transcription level.

(10) Add blank PBMC cells to the supernatant and go on being cultured in 5% CO2 incubator at 37° C. for 24 hours, centrifuged at 1000×g for 2 minutes, collect total mRNA from cells and reverse cDNA to detect CRP mRNA transcription level.

(11) Quantitative fluorescence PCR experiment was performed with IL-6 gene QPCR primers (SEQ ID NO: 63-SEQ ID NO: 64) and CRP gene QPCR primers (SEQ ID NO: 65-SEQ ID NO: 66). The reaction system was shown in Table 6. The internal reference Actin was used as the control group to verify the transcription of the mRNA.

Figure 14:
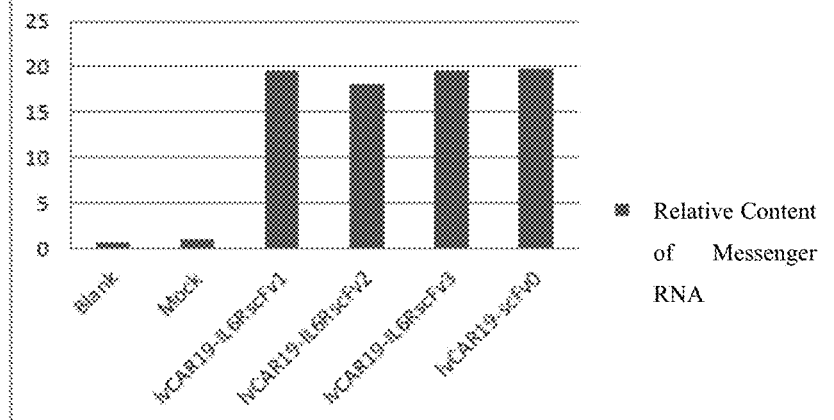
FIG. 14 is a schematic diagram of the change of mRNA transcription level after 12-hour co-culture of different effector cells with target cells in embodiment 3 of the invention.
Figure 15:
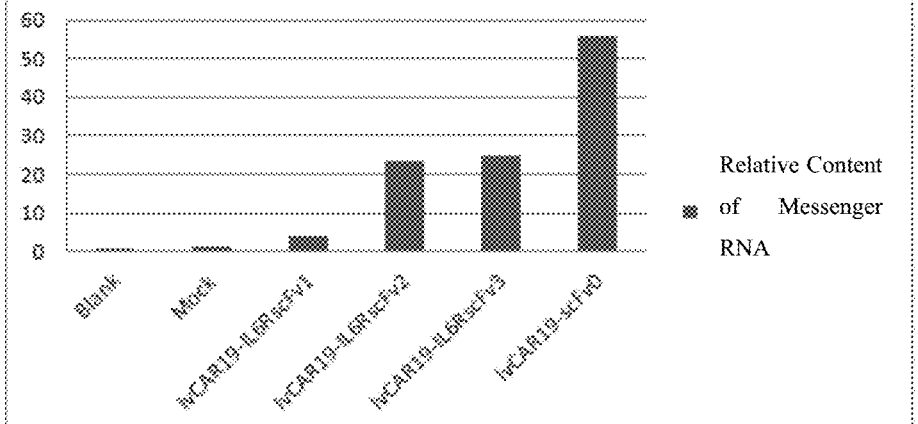
FIG. 15 is a schematic diagram of the change of CRPmRNA transcription level in PBMC after 12-hour culture in different groups of supernatant in embodiment 3 of the invention.

(12) RT-QPCR results showed that after incubation of PBMC transduced by 1vCAR19-IL6RscFv1, 1vCAR19-IL6RscFv2, 1vCAR19-IL6RscFv3 and 1vCAR19-scFv0 and target cells, mRNA level of IL-6 gene is significantly increased compared with Mock group and empty cell group, but mRNA level of IL-6 gene has no big difference among 1vCAR19-IL6RscFv1, 1vCAR19-IL6RscFv2, 1vCAR19-IL6RscFv3 and 1vCAR19-scFv0 (as shown in FIG. 14). Later, by detecting the mRNA transcription level of CRP genes in PBMC cells cultured in different groups of supernatant, it's found that the mRNA transcription level of CRP of the 1vCAR19-IL6RscFv1, 1vCAR19-IL6RscFv2 and 1vCAR19-IL6RscFv3 was significantly lower than that of the control virus 1vCAR19-scFv0, and the fall of the mRNA transcription level of CRP genes of 1vCAR19-IL6RscFv0 is the most obvious in the three groups (as shown in FIG. 15), indicating that 1vCAR19-IL6RscFv1, 1vCAR19-IL6RscFv2 and 1vCAR19-IL6RscFv3 all can effectively block the IL-6 signaling pathway (and 1vCAR19-IL6RscFv1 has the most obvious efficacy of blocking IL-6 signaling pathway), so as to effectively alleviate CRS clinically.

What is claimed is:

1. A CAR-T transgenic vector for alleviating cytokine release syndrome (CRS) by blocking IL6R, said vector comprising:
an AmpR sequence comprising ampicillin resistance gene having the sequence of SEQ ID NO. 1 for amplifying target bacterial strains;
a prokaryotic replicon pUC Ori sequence having the sequence of SEQ ID NO: 2 for plasmid replication;
a SV 40 Ori sequence of viral replicator having the sequence of SEQ ID NO: 3 for enhancing replication in eukaryotic cells;
an eWPRE enhanced posttranscriptional regulatory element of groundhog hepatitis B virus having the sequence of SEQ ID NO: 11 for enhancing the expression efficiency of transgene;
a human EF1α promoter having the sequence of SEQ ID NO. 12 for eukaryotic transcription of chimeric antigen receptor genes;
a lentivirus packaging cis-element for lentivirus packaging;
a nucleotide sequence encoding a humanized single chain antibody fragment of human IL6R, wherein the humanized single chain antibody fragment of the human IL6R is selected from the group consisting of (i) IL6RscFv1 encoded by the sequence of SEQ ID NO: 21, (ii) IL6RscFv2 encoded by the sequence of SEQ ID NO: 22 and (iii) IL6RscFv3 encoded by the sequence of SEQ ID NO: 23;
an IRES ribosome binding sequence having the sequence of SEQ ID NO. 25 for co-transcription and expression of proteins;
a nucleotide sequence having the sequence of SEQ ID NO 26 encoding IL-6 signal peptide;
a nucleotide sequence having the sequence of SEQ ID NO: 27 encoding human antibody $F_C$ segment; and
a nucleotide sequence encoding a second-generation chimeric antigen receptor (CAR) or a third generation CAR.

2. The CAR-T transgenic vector of claim 1, wherein the lentivirus packaging cis-element is a second-generation lentivirus vector, and the second-generation lentivirus vector comprises: a lentivirus 5 terminal LTR having the sequence of SEQ ID NO: 5, a lentivirus 3 terminal self-Inactivating LTR having the sequence of SEQ ID NO: 6, a Gag cis-element having the sequence of SEQ ID NO: 7, a RRE cis-element having the sequence of SEQ ID NO: 8, an env cis-element having the sequence of SEQ ID NO: 9, and a cPPT cis-elements having the sequence of SEQ ID NO: 10.

3. The CAR-T transgenic vector of claim 1, wherein the lentivirus packaging cis-element-is a third-generation lentivirus vector, and the third generation lentivirus vector comprises: a lentivirus 5 terminal LTR having the sequence of SEQ ID NO: 5, a lentivirus 3 terminal self-Inactivating LTR having the sequence of SEQ ID NO: 6, a Gag cis-element having the sequence of SEQ ID NO: 7, a RRE cis-element having the sequence of SEQ ID NO: 8, an env cis-element having the sequence of SEQ ID NO: 9, a cPPT cis-elements having the sequence of SEQ ID NO: 10, and a RSV promoter having the sequence of SEQ ID NO: 4.

4. The CAR-T transgenic vector of 1, wherein the chimeric antigen receptors of the second-generation CAR comprises: a CD8 leader chimeric receptor signal peptide encoded by the sequence of SEQ ID NO: 13, a CD19 single chain antibody fragment light chain VL encoded by the sequence of SEQ ID NO: 14, an Optimal Linker C encoded by the sequence of SEQ ID NO: 15, a CD19 single chain antibody fragment heavy chain VH encoded by the sequence of SEQ ID NO: 16, a CD8 Hinge chimeric receptor hinges encoded by the sequence of SEQ ID NO: 17, a CD8 transmembrane chimeric receptor transmembrane regions encoded by the sequence of SEQ ID NO: 18, a CD137 chimeric receptor costimulatory factors encoded by the sequence of SEQ ID NO: 19, and a TCR chimeric receptor T cell activation domains encoded by the sequence of SEQ ID NO: 20;
the chimeric antigen receptors of the third-generation CAR comprises: a CD8 leader chimeric receptor signal peptide encoded by the sequence of SEQ ID NO: 13, a CD19 single chain antibody fragment light chain VL encoded by the sequence of SEQ ID NO: 14, an Optimal Linker C encoded by the sequence of SEQ ID NO: 15, a CD19 single chain antibody fragment heavy chain VH encoded by the sequence of SEQ ID NO: 16, a CD8 Hinge chimeric receptor hinges encoded by the sequence of SEQ ID NO: 17, a CD8 transmembrane chimeric receptor transmembrane regions encoded by the sequence of SEQ ID NO: 18, a CD137 chimeric receptor costimulatory factors encoded by the sequence of SEQ ID NO: 19, a TCR chimeric receptor T cell activation domains encoded by the sequence of SEQ ID NO: 20, and a CD28 chimeric receptor costimulatory factors encoded by the sequence of SEQ ID NO: 28.

5. A preparation method of the CAR-T transgenic vector of claim 1, comprising the following steps:
(i) modifying a lentiviral skeleton plasmid to carry the ampR sequence containing ampicillin resistance gene having the sequence of SEQ ID NO: 1, the prokaryotic replicon pUC Ori sequence having the sequence of SEQ ID NO:2, the vims replicon SV40 Ori sequence having the sequence of SEQ ID NO:3, the lentiviral packaging cis-element for lentiviral packaging, and the eWPRE enhanced posttranscriptional regulatory element of the groundhog hepatitis B virus having the sequence of SEQ ID NO: 11;
(ii) combining the human EF1α promoter having the sequence of SEQ ID NO: 12 and the chimeric antigen receptors of the second-generation CAR or third-generation CAR for integrating recognition, transmission and initiation to form a second-generation CAR design scheme or a third-generation CAR design scheme; and cloning the second generation CAR design scheme or the third-generation CAR design scheme into lentivirus skeleton plasmids by enzymatic digestion, ligation and recombination reaction to obtain recombinant lentivirus plasmids designed by the second-generation CAR or the third generation CAR;
(iii) cloning the nucleotide sequence encoding humanized single-chain antibodies fragment IL6RscFv1, IL6RscFv2, or IL6RscFv3 of human IL-6R, the IRES ribosome binding sequence, the nucleotide sequence encoding IL6 signal peptide and the nucleotide sequence encoding human antibody Fc fragment into recombinant lentiviral plasmids respectively to obtain IL6R recombinant lentiviral plasmids pCAR19-IL6RscFv1, pCAR19-IL6RscFv2, or pCAR19-IL6RscFv3;
(iv) transfecting the IL6R recombinant lentiviral plasmid pCAR19-IL6RscFv1, pCAR19-IL6RscFv2, or pCAR19-IL6RscFv3 into HEK293T/17 cells with lentiviral packaging plasmids pPac-GP and pPac-R and membrane protein pEnv-G respectively; wherein after the recombinant lentiviral plasmids are transcribed and expressed in the HEK.293T/1 7 cells, and recombinant lentiviral vectors are packaged successfully are released into a supernatant of a HEK293T/17 cells culture medium; collecting the supernatant containing the recombinant lentiviral vectors; and (v) purifying the supernatants by column purification of filtration, adsorption and elution to obtain the recombinant lentiviral vector respectively.

6. The preparation method of claim 5, wherein in step (5), the step of the filtration comprises: controlling a volume of the supernatant from 200 ml to 2000 ml, a vacuum degree from −0.5 MPA to 0.9 MPA to prevent a loss of vectors caused by blockage; the step of the adsorption comprises: controlling a pH value of solution from 6 to 8, and preventing the recombinant lentiviral vectors from inactivating due to a change of pH; and the step of the elution comprises: controlling an ionic strength of eluent at 0.5 M-1.0 M, and preventing a change of the ionic strength from leading to incomplete elution or inactivation of the recombinant lentiviral vectors.

7. The preparation method of claim 5, wherein the lentivirus packaging cis-element is a second-generation lentivirus vector, and the second-generation lentivirus vector comprises: a lentivirus 5 terminal LTR having the sequence of SEQ ID NO: 5, a lentivirus 3 terminal self-Inactivating LTR having the sequence of SEQ ID NO: 6, a Gag cis-element having the sequence of SEQ ID NO: 7, a RRE cis-element having the sequence of SEQ ID NO: 8, an env cis-element having the sequence of SEQ ID NO: 9, and a cPPT cis-elements having the sequence of SEQ ID NO: 10.

8. The preparation method of claim 5, wherein the lentivirus packaging cis-element-is a third-generation lentivirus vector, and the third generation lentivirus vector comprises: a lentivirus 5 terminal LTR having the sequence of SEQ ID NO: 5, a lentivirus 3 terminal self-Inactivating LTR having the sequence of SEQ ID NO: 6, a Gag cis-element having the sequence of SEQ ID NO: 7, a RRE cis-element having the sequence of SEQ ID NO: 8, an env cis-element having the sequence of SEQ ID NO: 9, a cPPT cis-elements having the sequence of SEQ ID NO: 10, and a RSV promoter having the sequence of SEQ ID NO: 4.

9. The preparation method of claim 5, wherein the chimeric antigen receptors of the second-generation CAR comprises: a CD8 leader chimeric receptor signal peptide encoded by the sequence of SEQ ID NO: 13, a CD19 single chain antibody fragment light chain VL encoded by the sequence of SEQ ID NO: 14, an Optimal Linker C encoded by the sequence of SEQ ID NO: 15, a CD19 single chain antibody fragment heavy chain VH encoded by the sequence of SEQ ID NO: 16, a CD8 Hinge chimeric receptor hinges encoded by the sequence of SEQ ID NO: 17, a CD8 transmembrane chimeric receptor transmembrane regions encoded by the sequence of SEQ ID NO: 18, a CD137 chimeric receptor costimulatory factors encoded by the sequence of SEQ ID NO: 19, and a TCR chimeric receptor T cell activation domains encoded by the sequence of SEQ ID NO: 20;

the chimeric antigen receptors of the third-generation CAR comprises: a CD8 leader chimeric receptor signal peptide encoded by the sequence of SEQ ID NO: 13, a CD19 single chain antibody fragment light chain VL encoded by the sequence of SEQ ID NO: 14, an Optimal linker C encoded by the sequence of SEQ ID NO: 15, a CD19 single chain antibody fragment heavy chain VH encoded by the sequence of SEQ ID NO: 16, a CD8 Hinge chimeric receptor hinges encoded by the sequence of SEQ ID NO: 17, a CD8 transmembrane chimeric receptor transmembrane regions encoded by the sequence of SEQ ID NO: 18, a CD137 chimeric receptor costimulatory factors encoded by the sequence of SEQ ID NO: 19, a TCR chimeric receptor T cell activation domains encoded by the sequence of SEQ ID NO: 20, and a CD28 chimeric receptor costimulatory factors encoded by the sequence of SEQ ID NO: 28.

10. The preparation method of claim 7, wherein in step (5), the step of the filtration comprises: controlling a volume of the supernatant from 200 ml to 2000 ml, a vacuum degree from −0.5 MPA to 0.9 MPA to prevent a loss of vectors caused by blockage; the step of the adsorption comprises: controlling a pH value of solution from 6 to 8, and preventing the recombinant lentiviral vectors from inactivating due to a change of pH; and the step of the elution comprises: controlling an ionic strength of eluent at 0.5 M-1.0 M, and preventing a change of the ionic strength leading to incomplete elution or inactivation of the recombinant lentiviral vectors.

* * * * *